(12) United States Patent
Corona et al.

(10) Patent No.: US 12,004,947 B1
(45) Date of Patent: Jun. 11, 2024

(54) CONNECTING SKIRT FOR ATTACHING A LEAFLET TO A FRAME OF A PROSTHETIC HEART VALVE

(71) Applicant: EDWARDS LIFESCIENCES CORPORATION, Irvine, CA (US)

(72) Inventors: Jeanette Jasmine Corona, Anaheim, CA (US); Brendan Michael Dalbow, Huntington Beach, CA (US); Gil Senesh, Adi (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/316,056

(22) Filed: May 11, 2023

Related U.S. Application Data

(63) Continuation of application No. PCT/US2022/012873, filed on Jan. 19, 2022.

(Continued)

(51) Int. Cl.
*A61F 2/24* (2006.01)

(52) U.S. Cl.
CPC .......... *A61F 2/2415* (2013.01); *A61F 2/2412* (2013.01); *A61F 2220/0075* (2013.01)

(58) Field of Classification Search
CPC ........ A61F 2/24; A61F 2/2412; A61F 2/2415; A61F 2220/0075
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Dinah Baria
(74) *Attorney, Agent, or Firm* — Klarquist Sparkman, LLP; Sean Seung Kyu Kim

(57) ABSTRACT

Methods and assemblies for attaching leaflets to a frame of a prosthetic heart valve using a connecting skirt are disclosed. As one example, a prosthetic heart valve can include an annular frame comprising a plurality of struts and a valvular structure mounted within the frame and comprising a plurality of leaflets. A cusp edge portion of each leaflet can be connected to the frame by a connecting skirt, where each connecting skirt comprises a central portion and opposing side base portions on opposite sides of the central portion that are connected to each of and disposed between the frame and the cusp edge portion of the leaflet and each connecting skirt can further comprise side extension portions that extend outward from the cusp edge portion of the leaflet and across struts of the frame that are disposed between cusp edge portions of two adjacent leaflets.

20 Claims, 15 Drawing Sheets

Related U.S. Application Data

(60) Provisional application No. 63/139,514, filed on Jan. 20, 2021.

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eldenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eldenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | |
|---|---|---|
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Ellasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,096,781 B2 * | 8/2021 | Gurovich ............. A61F 2/2409 |
| 11,224,509 B2 | 1/2022 | Dasi et al. |
| 2001/0021872 A1 | 9/2001 | Balley et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishil |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Call et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |

(56) References Cited

FOREIGN PATENT DOCUMENTS

| | | |
|---|---|---|
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

Bailey, S. "Percutaneous Expandable Prosthetic Valves," Textbook of Interventional Cardiology vol. 2, 2nd Ed. pp. 1268-1276. 1994.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Wheatley, "Valve Prostheses," Operative Surgery, 4th ed. pp. 415-424. 1986.

\* cited by examiner

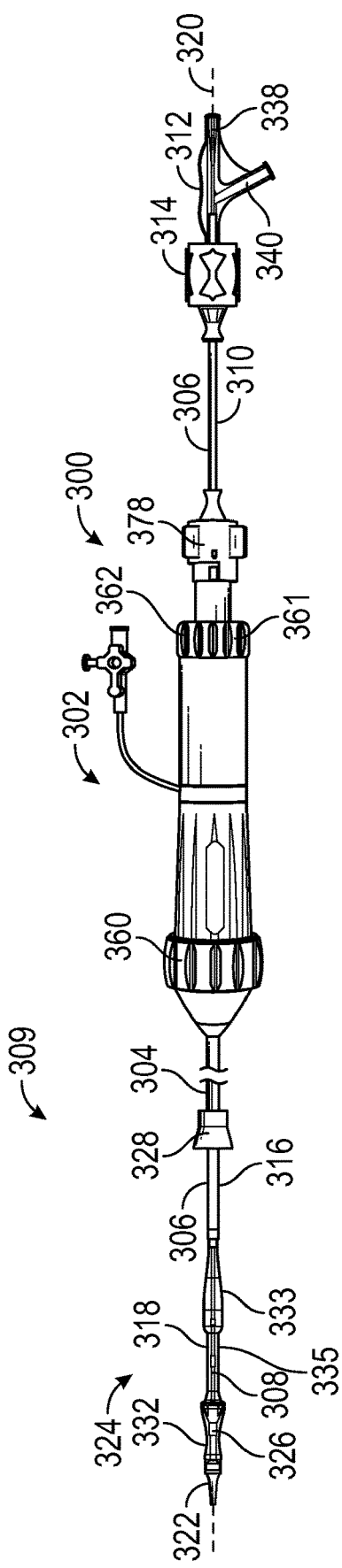
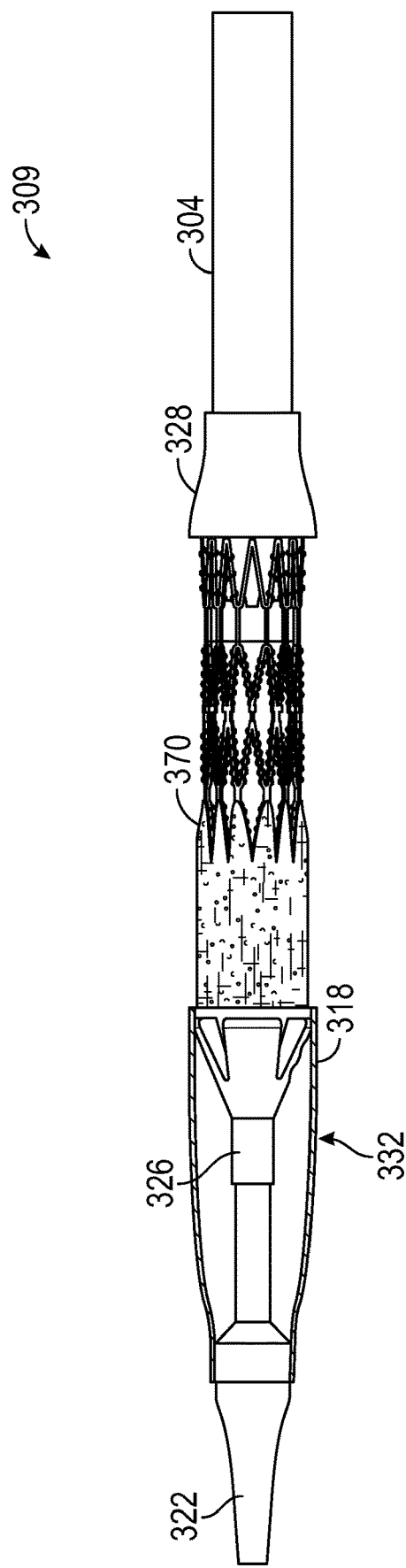
FIG. 4
FIG. 5

_US 12,004,947 B1_

CONNECTING SKIRT FOR ATTACHING A LEAFLET TO A FRAME OF A PROSTHETIC HEART VALVE

CROSS REFERENCE TO RELATED APPLICATIONS

This application is a continuation of PCT Application No. PCT/US2022/012873, filed Jan. 19, 2022, which claims the benefit of U.S. Provisional Patent Application No. 63/139,514, filed Jan. 20, 2021, both of which applications are incorporated herein by reference in their entirety.

FIELD

The present disclosure relates to prosthetic heart valves and to methods and assemblies for attaching leaflets to a frame of the prosthetic heart valve with one or more connecting skirts.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

In some examples, the prosthetic heart valve can include a radially expandable and compressible frame comprising a plurality of struts and a valvular structure mounted within and to the frame. The valvular structure can comprise a plurality of leaflets. In some examples, a cusp edge portion of each leaflet can be secured to the frame with a connecting skirt that is attached to the leaflet. In such arrangements, struts of the frame that are disposed between cusp edge portions of adjacent leaflets can be uncovered by material of the leaflet and connecting skirt.

When the prosthetic heart valve is radially compressed onto and around the inflatable balloon of the delivery apparatus, the uncovered struts, which can include apices at an inflow end of the frame, can come into direct contact with the balloon. As a result, the uncovered struts and apices can cause abrasion or degradation to the balloon. In some examples, this can result in reduced or inadequate inflation of the balloon when attempting to deploy the prosthetic heart valve at an implantation site using the delivery apparatus.

Accordingly, a need exists for improved prosthetic heart valves and methods for assembling a valvular structure to a frame of a prosthetic heart valve which can result in reduced contact between struts of the frame and a balloon of a delivery apparatus when the prosthetic heart valve is radially compressed onto the delivery apparatus, around the balloon.

SUMMARY

Described herein are examples of prosthetic heart valves including a frame and a valvular assembly arranged within and mounted to the frame and methods for assembling a prosthetic heart valve including a leaflet assembly. In some examples, the valvular assembly can comprise a plurality of leaflets, where each leaflet comprises opposing tabs on opposite sides of the leaflet and a cusp edge portion between the tabs. For each leaflet, the cusp edge portion can be connected to the frame by a connecting skirt. The connecting skirt can include a central portion, opposing side base portions on opposite sides of the central portion, and side extension portions that extend outward from respective side base portions. The central portion and opposing side base portions of the connecting skirt can be connected to each of the frame and the cusp edge portion of the leaflet and the side extension portions can extend across struts of the frame that are disposed between cusp edge portions of two adjacent leaflets.

In one representative example, a prosthetic heart valve comprises an annular frame comprising an inflow end and an outflow end and being radially collapsible and expandable between a radially collapsed configuration and a radially expanded configuration, wherein the frame comprises a plurality of struts. The prosthetic heart valve further comprises a valvular structure mounted within the frame and comprising a plurality of leaflets, wherein each leaflet comprises opposing tabs on opposite sides of the leaflet and a cusp edge portion between the tabs. The cusp edge portion of each leaflet is connected to the frame by a connecting skirt, wherein each connecting skirt comprises a central portion and opposing side base portions on opposite sides of the central portion that are connected to each of and disposed between the frame and the cusp edge portion of the leaflet, and wherein each connecting skirt further comprises side extension portions that extend outward from the cusp edge portion of the leaflet and across struts of the frame that are disposed between cusp edge portions of adjacent leaflets.

In another representative example, a prosthetic heart valve comprises an annular frame comprising an inflow end and an outflow end and being radially collapsible and expandable between a radially collapsed configuration and a radially expanded configuration, wherein the frame comprises a plurality of struts. The prosthetic heart valve further comprises a valvular structure mounted within the frame and comprising a plurality of leaflets, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame. The prosthetic heart valve further comprises a plurality of connecting skirts, each connecting skirt comprising side base portions and a central portion connected to each of the cusp edge portion of a corresponding leaflet of the plurality of leaflets and struts of the frame, each connecting skirt further comprising side extension portions that extend outward and away from the cusp edge portion, wherein each side extension portion of each connecting skirt extends across struts of the frame, between cusp edge portions of adjacent leaflets and connects to an adjacent side extension portion of an adjacent connecting skirt.

In another representative example, a method of assembling a prosthetic heart valve comprising a plurality of leaflets, comprises forming a plurality of leaflet assemblies with the plurality of leaflets. Each leaflet assembly is formed by securing a central portion and side base portions of a connecting skirt to a cusp edge portion of a leaflet, wherein each connecting skirt comprises two side portions, one arranged on either side of the central portion, and wherein each side portion comprises a corresponding side base portion of the side base portions and a side extension portion extending outward and away from the corresponding side base portion. The method further comprises securing each connecting skirt to a frame of the prosthetic heart valve, the frame comprising a plurality of interconnected and angled struts, the securing including: securing the central portion and side base portions of the connecting skirt to a first portion of struts of the plurality of struts and extending each side extension portion of the connecting skirt across a second portion of struts of the plurality of struts that are disposed between cusp edge portions of adjacent leaflets and securing each side extension portion to an adjacent side extension portion of an adjacent connecting skirt.

In another representative example, a prosthetic heart valve comprises: an annular frame comprising an inflow end and an outflow end and being radially collapsible and expandable between a radially collapsed configuration and a radially expanded configuration, wherein the frame comprises a plurality of struts. The prosthetic heart valve further comprises a valvular structure mounted within the frame and comprising a plurality of leaflets, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame. The prosthetic heart valve further comprises a plurality of connecting skirts, each connecting skirt comprising a base portion connected to each of the cusp edge portion of a corresponding leaflet of the plurality of leaflets and struts of the frame, each connecting skirt further comprising extension portions that extend outward and away from the cusp edge portion and cover inner surfaces of struts of the frame disposed between cusp edge portions of adjacent leaflets. The prosthetic heart valve further comprises an outer sealing member mounted around an outer surface of the frame and secured to the struts of the frame and the plurality of connecting skirts, the plurality of connecting skirts mounted around an inner surface of the frame.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, claims, and accompanying figures.

BRIEF DESCRIPTION OF THE DRAWINGS

FIG. 4 is a side view of an example of a delivery apparatus configured to deliver and implant a radially expandable prosthetic heart valve at an implantation site.

FIG. 5 is a side view of the distal end portion of the delivery apparatus of FIG. 4 with a prosthetic heart valve mounted on a valve mounting portion of the delivery apparatus.

DETAILED DESCRIPTION

General Considerations

Figure 1A:
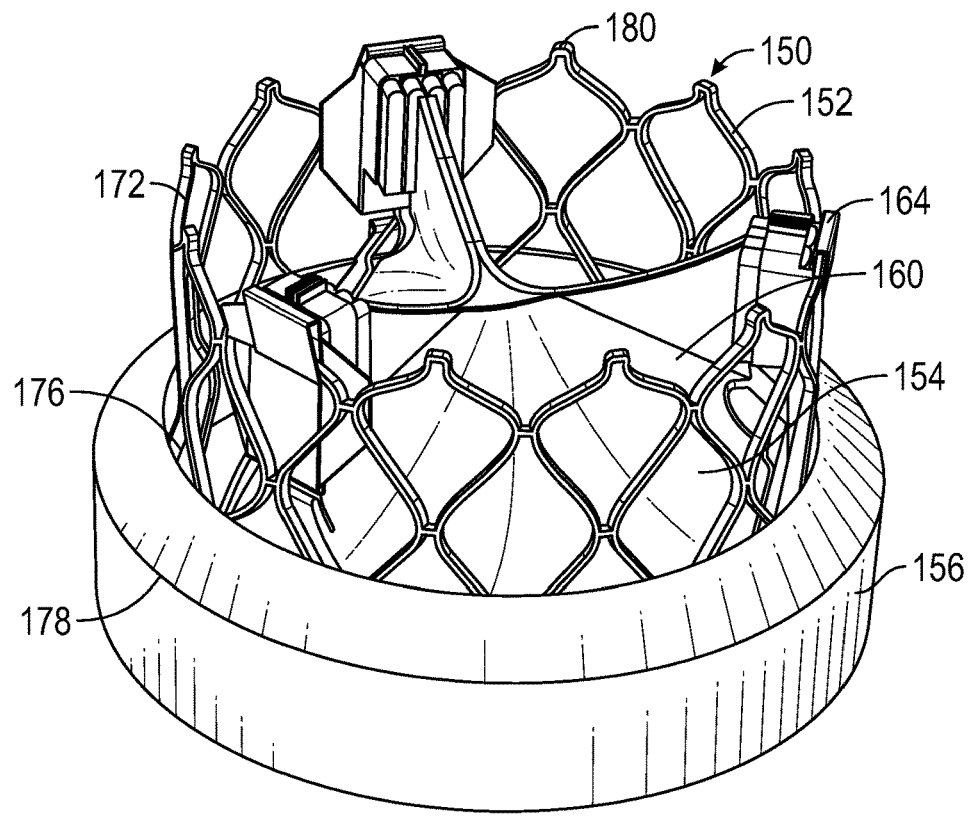
FIG. 1A is a perspective view of a prosthetic heart valve, according to one example.

For purposes of this description, certain aspects, advantages, and novel features of examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Examples of the Disclosed Technology

Described herein are examples of prosthetic heart valves, leaflet assemblies for prosthetic heart valves, connecting skirts, and methods for assembling leaflets assemblies and valvular structures to a frame of the prosthetic heart valve using one or more connecting skirts. The prosthetic heart valves can comprise a frame and a valvular structure attached to the frame, the valvular structure comprising a plurality of leaflets. In some examples, a connecting skirt can be secured to a cusp edge portion of a leaflet of the valvular structure. The portion of the connecting skirt secured to the cusp edge portion of the leaflet can then be secured to struts of the frame of the prosthetic heart valve, thereby securing the cusp edge portion of the leaflet to the frame, proximate to an inflow end of the frame. The connecting skirt can include side extension portions that extend outward from the cusp edge portion of the leaflet and across struts of the frame that are arranged between cusp edge portions of adjacent leaflets, when the connecting skirt is attached to struts of the frame. In this way, the side extension portions can cover inner surfaces of struts of the frame and/or apices of the frame at the inflow end of the frame.

Prosthetic valves disclosed herein can be radially compressible and expandable between a radially compressed configuration and a radially expanded configuration. Thus, the prosthetic valves can be crimped on or retained by an implant delivery apparatus in the radially compressed configuration during delivery, and then expanded to the radially expanded configuration once the prosthetic valve reaches the implantation site. It is understood that the prosthetic valves disclosed herein may be used with a variety of implant delivery apparatuses and can be implanted via various delivery procedures, examples of which will be discussed in more detail later. In some examples, the prosthetic valve can be deployed from the delivery apparatus at the implantation site (e.g., a native valve of a heart) via inflating an inflatable balloon of the delivery apparatus. When radially compressed onto the inflatable balloon of the delivery apparatus, inner surfaces of the frame of the prosthetic valve can face the balloon.

FIG. 1A shows an exemplary prosthetic valve 150, according to one example. Any of the prosthetic valves disclosed herein are adapted to be implanted in the native aortic annulus, although in other examples they can be adapted to be implanted in the other native annuluses of the heart (the pulmonary, mitral, and tricuspid valves). The disclosed prosthetic valves also can be implanted within vessels communicating with the heart, including a pulmonary artery (for replacing the function of a diseased pulmonary valve, or the superior vena cava or the inferior vena cava (for replacing the function of a diseased tricuspid valve) or various other veins, arteries and vessels of a patient. The disclosed prosthetic valves also can be implanted within a previously implanted prosthetic valve (which can be a prosthetic surgical valve or a prosthetic transcatheter heart valve) in a valve-in-valve procedure.

In some examples, the disclosed prosthetic valves can be implanted within a docking or anchoring device that is implanted within a native heart valve or a vessel. For example, in one example, the disclosed prosthetic valves can be implanted within a docking device implanted within the pulmonary artery for replacing the function of a diseased pulmonary valve, such as disclosed in U.S. Publication No. 2017/0231756, which is incorporated by reference herein. In another example, the disclosed prosthetic valves can be implanted within a docking device implanted within or at the native mitral valve, such as disclosed in PCT Publication No. WO2020/247907, which is incorporated herein by reference. In another example, the disclosed prosthetic valves can be implanted within a docking device implanted within the superior or inferior vena cava for replacing the function of a diseased tricuspid valve, such as disclosed in U.S. Publication No. 2019/0000615, which is incorporated herein by reference.

FIG. 1A is a perspective view of a prosthetic heart valve (e.g., prosthetic valve) 150, according to one example. The illustrated prosthetic valve is adapted to be implanted in the native aortic annulus, although in other examples it can be adapted to be implanted in the other native annuluses of the heart (e.g., the pulmonary, mitral, and tricuspid valves). The prosthetic valve can also be adapted to be implanted in other tubular organs or passageways in the body.

Figure 1B:
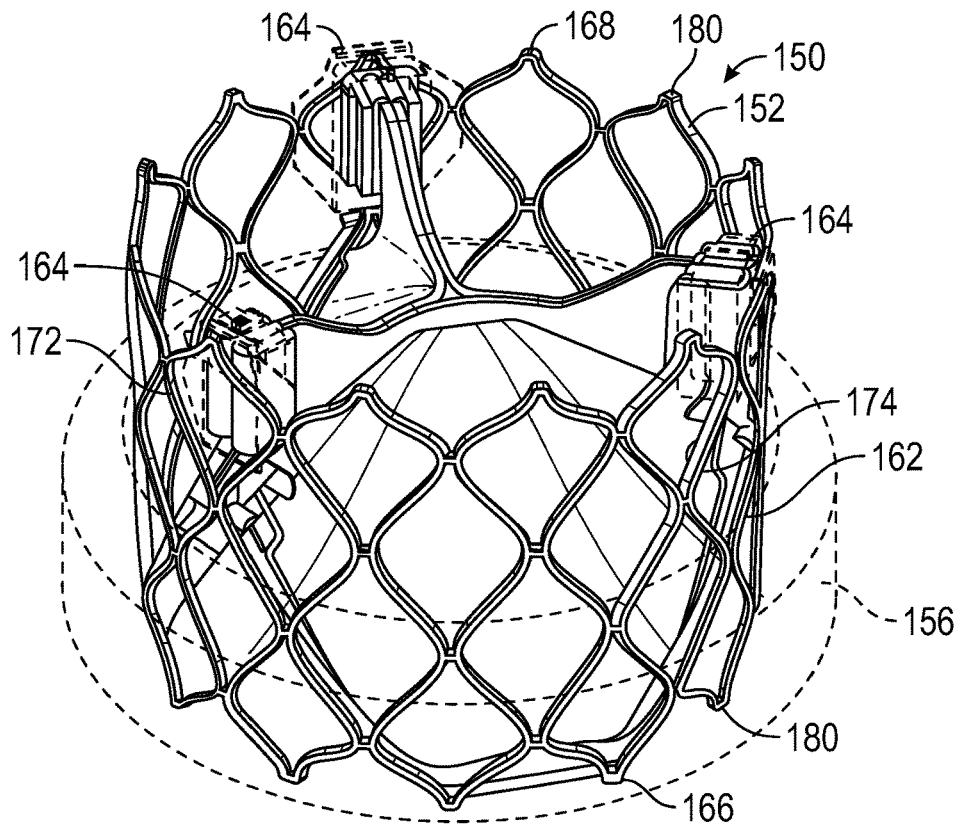
FIG. 1B is a perspective view of the prosthetic valve of FIG. 1A with the components on the outside of the frame shown in transparent lines for purpose of illustration.

The prosthetic valve 150 can have three main components: a stent or frame, 152, a valvular structure 154, and a sealing member 156. FIG. 1B is a perspective view of the prosthetic valve 150 with the components on the outside of the frame 152 (including the sealing member 156) shown in transparent lines for purposes of illustration. The prosthetic valve 150 can have an inflow end 166 and an outflow end 168.

The valvular structure 154 can comprise three leaflets 160, collectively forming a leaflet structure, which can be arranged to collapse in a tricuspid arrangement, although in other examples there can be greater or fewer number of leaflets (e.g., one or more leaflets 160). In some examples, the leaflets 160 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

Each leaflet 160 can be coupled to the frame 152 along its inflow edge 162 (the lower edge in the figures; also referred to as "cusp edges") and at commissures 164 of the valvular structure 154 where adjacent portions (e.g., commissure tabs) of two leaflets are connected to each other. In some examples, the commissures 164 can comprise an attachment member (e.g., comprising fabric, flexible polymer, or the like) arranged across a cell (e.g., commissure cell) of the frame 152, the cell formed by struts of the frame. The attachment member can be secured to the struts of the frame forming the cell and the adjacent portions of the two leaflets can be connected to the attachment member to form the commissure 164 (e.g., as shown in FIGS. 2, and 23-25, as described further below).

Figure 2:
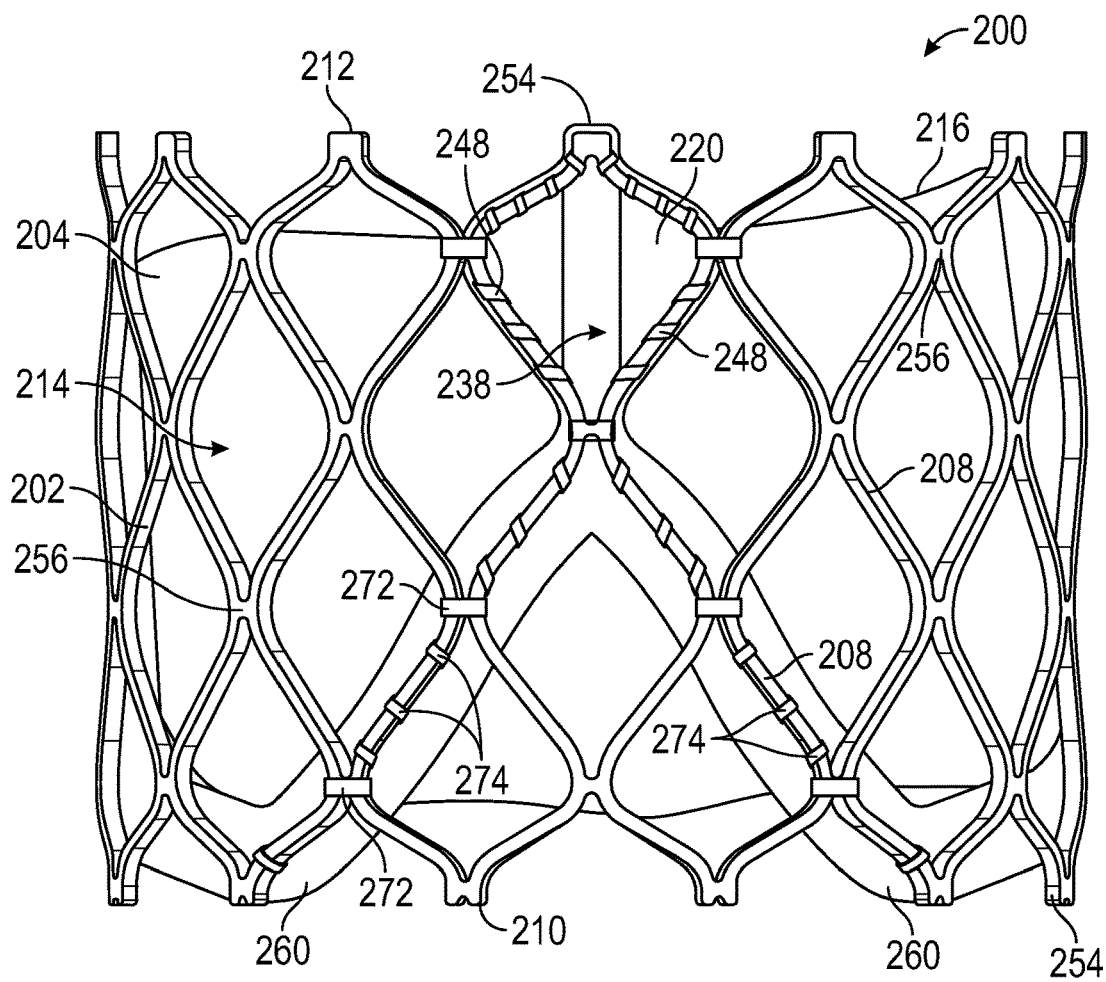
FIG. 2 is a side view of a prosthetic heart valve with components on an outside of a frame of the prosthetic heart valve removed, according to another example, which includes a connecting skirt coupling a cusp edge portion of a leaflet to the frame of the prosthetic heart valve.
Figure 3:
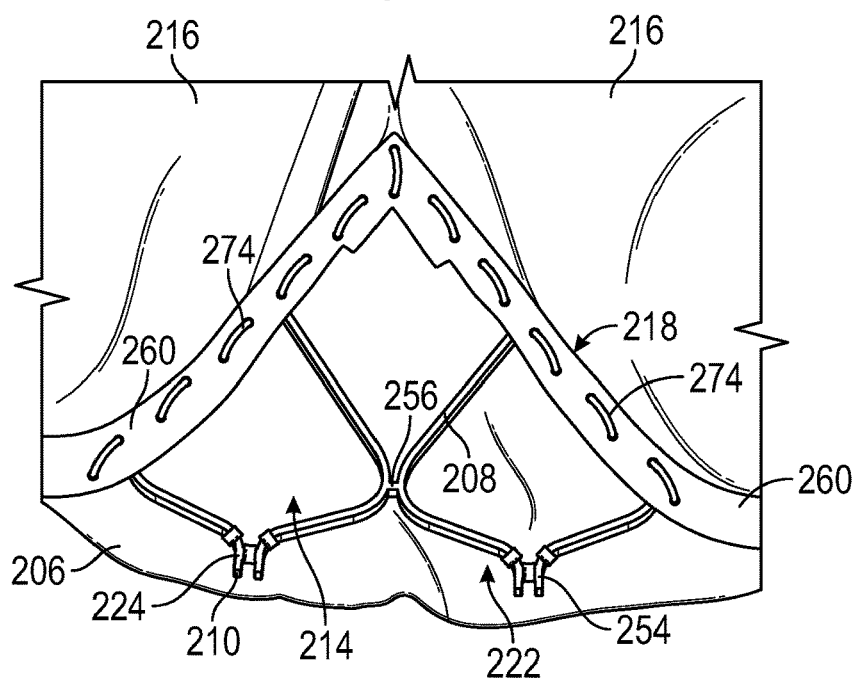
FIG. 3 is a partial, detail view of an interior surface of the prosthetic heart valve of FIG. 2.

In some examples, a reinforcing element or connecting skirt, such as a fabric strip, can be connected directly to the cusp edges of the leaflets and to the struts of the frame to couple the cusp edges of the leaflets to the frame (e.g., as shown in FIGS. 2 and 3, as described further below).

The frame 152 can be made of any of various suitable plastically-expandable materials (e.g., stainless steel, etc.) or self-expanding materials (e.g., nickel titanium alloy (NiTi), such as nitinol), as known in the art. When constructed of a plastically-expandable material, the frame 152 (and thus the prosthetic valve 150) can be crimped to a radially collapsed configuration on a delivery apparatus (e.g., catheter) and then expanded inside a patient by an inflatable balloon or equivalent expansion mechanism. When constructed of a self-expandable material, the frame 152 (and thus the prosthetic valve 150) can be crimped to a radially collapsed configuration and restrained in the collapsed configuration by insertion into a sheath or equivalent mechanism of a delivery apparatus. Once inside the body, the prosthetic valve can be advanced from the delivery sheath, which allows the prosthetic valve to expand to its functional size.

Suitable plastically-expandable materials that can be used to form the frame 152 include, without limitation, stainless steel, a biocompatible, high-strength alloys (e.g., a cobalt-chromium or a nickel-cobalt-chromium alloys), polymers, or combinations thereof. In particular examples, frame 152 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight.

The frame 152 in the illustrated example comprises a plurality of circumferentially extending rows of angled struts 172 defining rows of open cells, or openings, 174 of the frame. The frame 152 can have a cylindrical or substantially cylindrical shape having a constant diameter from the inflow end 166 to the outflow end 168 of the frame 152 as shown, or the frame 152 can vary in diameter along the height of the frame, as disclosed in U.S. Patent Publication No. 2012/0239142, which is incorporated herein by reference.

The frame 152, at each of the inflow end 166 and the outflow end 168, may comprise a plurality of apices 180 spaced apart from one another around a circumference of the frame 152.

The sealing member 156 in the illustrated example is mounted on the outside of the frame 152 and functions to create a seal against the surrounding tissue (e.g., the native leaflets and/or native annulus) to prevent or at least minimize paravalvular leakage. The sealing member 156 can comprise an inner layer 176 (which can be in contact with the outer surface of the frame 152) and an outer layer 178. The sealing member 156 can be connected to the frame 152 using suitable techniques or mechanisms. For example, the sealing member 156 can be sutured to the frame 152 via sutures that can extend around the struts 172 and through the inner layer 176. In alternative examples, the inner layer 176 can be mounted on the inner surface of the frame 152, while the outer layer 178 is on the outside of the frame 152.

The outer layer 178 can be configured or shaped to extend radially outward from the inner layer 176 and the frame 152 when the prosthetic valve 150 is deployed. When the prosthetic valve is fully expanded outside of a patient's body, the outer layer 178 can expand away from the inner layer 176 to create a space between the two layers. Thus, when implanted inside the body, this allows the outer layer 178 to expand into contact with the surrounding tissue.

Additional details regarding the prosthetic valve 150 and its various components are described in U.S. Patent Publication No. 2018/0028310, which is incorporated herein by reference.

FIG. 2 is a side view of a prosthetic heart valve 200, according to another example. The prosthetic heart valve 200 can be similar to the prosthetic valve 150 of FIGS. 1A and 1B. For example, the prosthetic heart valve 200 can comprise a frame 202 and a valvular structure 204 which can be the same or similar to the frame 152 and valvular structure 154 of the prosthetic valve 150. For example, the frame 202 and the valvular structure 204 can comprise similar materials and/or have a similar geometry to the frame 152 and valvular structure 154, respectively, of the prosthetic valve 150, as described above with reference to FIGS. 1A and 1B.

In FIG. 2, the exterior of the frame 202 is shown with no sealing member arranged around the frame, thereby providing a view of the components coupling the valvular structure 204 to the frame 202. However, in some examples, the prosthetic heart valve 200 can include an outer sealing member (e.g., outer skirt) arranged around and coupled to an outer surface of the frame 202, such as the sealing member 156 shown in FIG. 1A.

For example, FIG. 3 is a partial, detail view of an interior surface of the prosthetic heart valve 200, showing an outer sealing member 206 arranged around an outer surface of the frame 202. Thus, FIG. 2 is an exterior view and FIG. 3 is an interior view of the prosthetic heart valve 200.

Similar to the frame 152 of the prosthetic valve 150, the frame 202 of the prosthetic heart valve 200 comprises a plurality of angled and interconnected struts 208. As shown in FIG. 2, the struts 208 can be arranged into a plurality of circumferentially extending rows of angled struts 208 that are disposed between an inflow end 210 and an outflow end 212 of the frame 202. The rows of struts 208 define rows of cells or openings (e.g., open cells) 214 of the frame 202. The frame 202, at each of the inflow end 210 and the outflow end 212, can comprise a plurality of apices 254 spaced apart from one another around a circumference of the frame 202. The apices 254 can be formed by the intersection of struts 208 at the inflow end 210 and the outflow end 212. Further, the frame 202 can include a plurality of strut junctions 256 formed by the intersection of struts 208 at location on the frame 202 between the inflow end 210 and the outflow end 212.

As shown in FIG. 2, each leaflet 216 of the valvular structure 204 can be coupled to the frame 202 along its inflow edge (also referred to as "cusp edges") and at commissures 238 of the valvular structure 204 where adjacent portions (e.g., commissure tabs) of two leaflets are connected to each other. In some examples, as shown in FIG. 2 and described further below, the commissures 238 can comprise an attachment member 220 (e.g., comprising fabric, flexible polymer, or the like) arranged across a cell 214 (e.g., commissure cell) of the frame 202. The attachment member 220 can be secured to the struts 208 of the frame 202 forming the cell 214 via stitching or sutures 248. Further, the adjacent portions of the two leaflets 216 can be connected to the attachment member 220 to form the commissure 238 (e.g., as shown in FIG. 2 and as described further below with reference to FIGS. 7 and 23-25).

In some examples, as shown in FIGS. 2 and 3, cusp edges 218 of the leaflets 216 can be coupled (e.g., secured) to the frame 202 with a connecting skirt (or member) 260. For example, in some examples, the cusp edge 218 of each leaflet 216 can be connected directly to a corresponding (e.g., individual) connecting skirt 260. Each connecting skirt 260 (e.g., one for each leaflet 216) can then be connected directly to the struts 208 of the frame 202, thereby coupling the cusp edges 218 of the leaflets 216 to the frame. In other examples, the connecting skirt 260 can be a single piece of material that is connected to all of the leaflets 216.

For example, as shown in FIG. 2, the connecting skirts 260 can be secured to strut junctions 256 by first sutures 272 and can be further connected, along their length, to struts 208 by second sutures (such as in the form of whip stitches) 274.

As shown in FIG. 3, a portion of the struts 208 of the frame 202 and a portion of the apices 254 at the inflow end 210 are exposed on an inside of the frame 202, at locations between adjacent leaflets 216 and connecting skirts 260.

FIGS. 4 and 5 show a delivery apparatus 300, according to an example, that can be used to implant an expandable prosthetic heart valve (e.g., prosthetic valve 150 of FIGS. 1A and 1B and/or prosthetic heart valve 200 of FIGS. 2 and 3), or another type of expandable prosthetic medical device (such as a stent). In some examples, the delivery apparatus 300 is specifically adapted for use in introducing a prosthetic valve into a heart.

The delivery apparatus 300 in the illustrated example of FIGS. 4 and 5 is a balloon catheter comprising a handle 302 and a steerable, outer shaft 304 extending distally from the handle 302 (FIG. 4). The delivery apparatus 300 can further comprise an intermediate shaft 306 (which can also be referred to as a balloon shaft) that extends proximally from the handle 302 (FIG. 4) and distally from the handle 302, the portion extending distally from the handle 302 also extending coaxially through the outer shaft 304. Additionally, the delivery apparatus 300 can further comprise an inner shaft 308 extending distally from the handle 302 coaxially through the intermediate shaft 306 and the outer shaft 304 (FIG. 4) and proximally from the handle 302 coaxially through the intermediate shaft 306.

The outer shaft 304 and the intermediate shaft 306 can be configured to translate (e.g., move) longitudinally, along a central longitudinal axis 320 of the delivery apparatus 300, relative to one another to facilitate delivery and positioning of a prosthetic valve at an implantation site in a patient's body.

The intermediate shaft 306 can include a proximal end portion 310 that extends proximally from a proximal end of the handle 302, to an adaptor 312 (FIG. 4). In some examples, a rotatable knob 314 can be mounted on the proximal end portion 310 (FIG. 4) and can be configured to rotate the intermediate shaft 306 around the central longitudinal axis 320 of the delivery apparatus 300 and relative to the outer shaft 304.

The adaptor 312 can include a first port 338 configured to receive a guidewire therethrough and a second port 340 configured to receive fluid (e.g., inflation fluid) from a fluid source. The second port 340 can be fluidly coupled to an inner lumen of the intermediate shaft 306.

The intermediate shaft 306 can further include a distal end portion 316 that extends distally beyond a distal end of the outer shaft 304 (FIG. 4) when a distal end of the outer shaft 304 is positioned away from an inflatable balloon 318 of the delivery apparatus. A distal end portion of the inner shaft 308 can extend distally beyond the distal end portion 316 of the intermediate shaft 306 (FIG. 4).

The balloon 318 can be coupled to the distal end portion 316 of the intermediate shaft 306. For example, in some examples, a proximal end portion of the balloon 318 can be coupled to and/or around a distal end of the intermediate shaft 306 (FIG. 4).

The balloon 318 can comprise a distal end portion (or section) 332, a proximal end portion (or section) 333, and an intermediate portion (or section) 335, the intermediate portion 335 disposed between the distal end portion 332 and the proximal end portion 333 (FIG. 4).

In some examples, a distal end of the distal end portion 332 of the balloon 318 can be coupled to a distal end of the delivery apparatus 300, such as to a nose cone 322 (as shown in FIGS. 4 and 5), or to an alternate component at the distal end of the delivery apparatus 300 (e.g., a distal shoulder). In some examples, the intermediate portion 335 of the balloon 318 can overlay a valve mounting portion 324 of a distal end portion 309 of the delivery apparatus 300, the distal end portion 332 can overly a distal shoulder 326 of the delivery apparatus 300, and the proximal end portion 333 can surround a portion of the inner shaft 308. The valve mounting portion 324 and the intermediate portion 335 of the balloon 318 can be configured to receive a prosthetic heart valve 370 in a radially compressed state, as shown in FIG. 5. In some examples, the prosthetic heart valve 370 shown in FIG. 5 can be one of valve 150 of FIGS. 1A and 1B or valve 200 of FIGS. 2 and 3.

In some examples, rotation of the intermediate shaft 306 can result in rotation of the balloon 318 and the prosthetic valve mounted thereon for rotational positioning of the prosthetic valve relative to the native anatomy at the target implantation site.

The balloon shoulder assembly is configured to maintain the prosthetic heart valve or other medical device at a fixed position on the balloon 318 during delivery through the patient's vasculature. The balloon shoulder assembly can include a distal shoulder 326 (FIGS. 4 and 5) arranged within the distal end portion 332 of the balloon 318 and coupled to the distal end portion of the inner shaft 308. The distal shoulder 326 can be configured to resist movement of the prosthetic valve or other medical device mounted on the valve mounting portion 324 distally, in an axial direction (e.g., along central longitudinal axis 320), relative to the balloon 318.

The outer shaft 304 can include a distal tip portion 328 mounted on its distal end (FIGS. 4 and 5). The outer shaft 304 and the intermediate shaft 306 can be translated axially relative to one another to position the distal tip portion 328 adjacent to a proximal end of the valve mounting portion 324, when a prosthetic valve is mounted in the radially compressed state on the valve mounting portion 324 and during delivery of the prosthetic valve to the target implantation site (as shown in FIG. 5). As such, the distal tip portion 328 can be configured to resist movement of the prosthetic valve relative to the balloon 318 proximally, in the axial direction, relative to the balloon 318, when the distal tip portion 328 is arranged adjacent to a proximal side of the valve mounting portion 324 (FIG. 5).

In some examples, the nose cone 322 can be disposed distal to and be coupled to the distal shoulder 326. In some examples, the nose cone 322 can be coupled to the distal end portion of the inner shaft 308.

In some examples, an annular space can be defined between an outer surface of the inner shaft 308 and an inner surface of the intermediate shaft 306. In some examples, the annular space can be referred to as an inner lumen of the intermediate shaft 306. In some examples, the annular space can be configured to receive fluid from a fluid source via the second port 340 of the adaptor 312 (e.g., the annular space is in fluid communication with the second port 340 of the adaptor 312). The annular space can be fluidly coupled to a fluid passageway formed between the outer surface of the distal end portion of the inner shaft 308 and an inner surface of the balloon 318. As such, fluid from the fluid source can flow to the balloon 318 to inflate the balloon 318 and radially expand and deploy the prosthetic valve (e.g., prosthetic valve 370 shown in FIG. 5).

An inner lumen of the inner shaft 308 can be configured to receive a guidewire therethrough, for navigating the distal end portion 309 of the delivery apparatus 300 to the target implantation site. As introduced above, the first port 338 of the adaptor 312 can be coupled to the inner lumen and configured to receive the guidewire. For example, the distal end portion 309 of the delivery apparatus 300 can be advanced over the guidewire, to the target implantation site.

As shown in FIG. 4, the handle 302 can include a steering mechanism configured to adjust the curvature of the distal end portion 309 of the delivery apparatus 300. In the illustrated example, for example, the handle 302 includes an adjustment member, such as the illustrated rotatable knob 360, which in turn is operatively coupled to the proximal end portion of a pull wire. The pull wire can extend distally from the handle 302 through the outer shaft 304 and has a distal end portion affixed to the outer shaft 304 at or near the distal end of the outer shaft 304. Rotating the knob 360 can increase or decrease the tension in the pull wire, thereby adjusting the curvature of the distal end portion 309 of the delivery apparatus 300. Further details on steering or flex mechanisms for the delivery apparatus can be found in U.S. Pat. No. 9,339,384, which is incorporated by reference herein.

The handle 302 can include one or more additional adjustment mechanisms. For example, in some examples, the handle 302 can include an adjustment mechanism 361 including an adjustment member, such as the illustrated rotatable knob 362. The adjustment mechanism 361 can be configured to adjust the axial position of the intermediate shaft 306 relative to the outer shaft 304. In some examples, the handle 302 can further include a locking mechanism, which can include a rotatable knob 379, the locking mechanism configured to retain (e.g., lock) the position of the intermediate shaft 306 relative to the handle 302 and allow for fine positioning of the prosthetic valve 370 at the implantation site.

Figure 6:
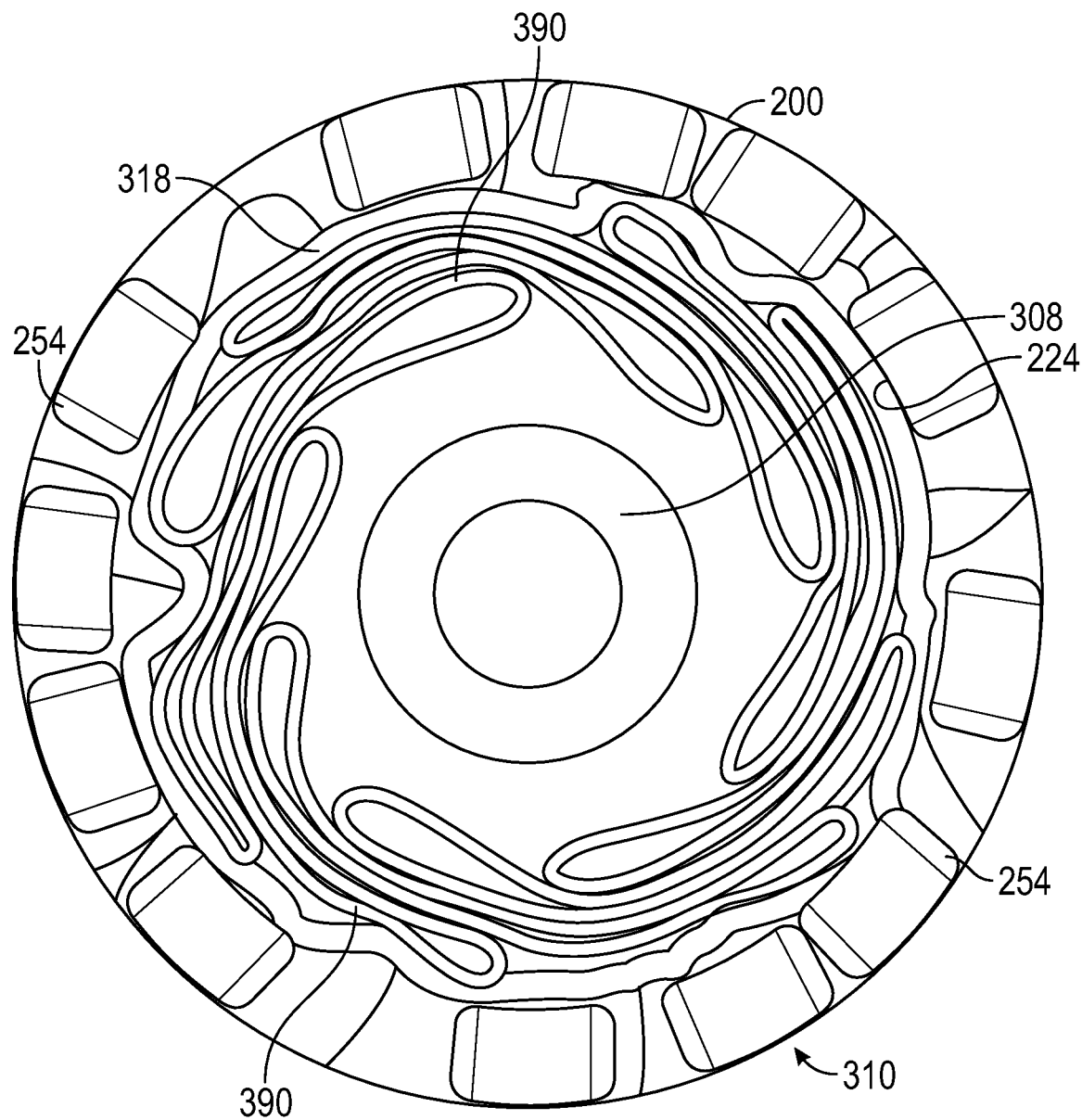
FIG. 6 is a cross-sectional view of the prosthetic heart valve of FIG. 2, radially compressed onto and mounted around an inflatable balloon of a delivery apparatus.

FIG. 6 is a cross-sectional view of the prosthetic heart valve 200 (FIGS. 2 and 3) radially compressed onto and mounted around the balloon 318, on the distal end portion 309 of the delivery apparatus 300. Specifically, the cross-sectional view of FIG. 6 is taken at the inflow end 210 of the frame 202. Thus, the apices 254 of the frame 202, at the inflow end 210, are seen in FIG. 6.

As shown in FIG. 6, the balloon 318 is wrapped and folded around the inner shaft 308, at the valve mounting portion 324 of the delivery apparatus 300. In some examples, as shown in FIG. 6, the balloon 318 includes a plurality of overlapping pleats or folds 390 when in its deflated configuration and when the prosthetic heart valve 200 is mounted on and radially compressed around the balloon 318. The balloon 318 can be folded in such a way that the pleats 390 result in a minimized folded balloon diameter (e.g., in its deflated configuration) which can reduce a diameter of the radially compressed prosthetic valve 200 when crimped thereon.

As shown in in FIGS. 2 and 3 and described above, an inner surface 224 (e.g., the surface facing an interior of the valve 200 and a central longitudinal axis of the valve 200) of the apices 254 and a portion of the struts 208 disposed between where adjacent connecting skirts 260 are connected to the frame 202 are exposed (e.g., not covered by skirt or leaflet material). For example, as shown in FIG. 3, exposed portions 222 of the frame 202 have an uncovered inner surface 224.

Thus, when crimped or radially compressed around the balloon 318, as shown in FIG. 6, the inner surface 224 of at least a portion of the apices 254 at the inflow end 210 of the frame 202 can directly contact the balloon 318. As a result, this may cause abrasion or degradation to the balloon 318, thereby resulting in reduced or inadequate inflation of the balloon 318 when attempting to deploy the prosthetic heart valve 200 at the implantation site.

FIGS. 7-12 show an assembled prosthetic heart valve 400 (FIGS. 7 and 12) and individual components of the prosthetic heart valve 400 (FIGS. 8-11), according to another example. FIGS. 13-25 show a method of assembling the components of the prosthetic heart valve 400 to form the assembled prosthetic heart valve 400. FIG. 26 is a cross-sectional view of the prosthetic heart valve 400 radially compressed onto and around the balloon 318 of the delivery apparatus 300.

The prosthetic heart valve 400 can be similar to the prosthetic valve 200 of FIGS. 2 and 3. However, the prosthetic heart valve 400 is configured such that abrasion or degradation of the balloon is reduced or prevented when the prosthetic heart valve 400 is radially compressed onto the balloon of the delivery apparatus.

For example, the prosthetic heart valve 400 can comprise the frame 202 and the valvular structure 204 connected to the frame 202, as described above. The prosthetic heart valve 400 can have a central longitudinal axis 402 arranged through a center of an interior of the frame 202. The frame 202 of the prosthetic heart valve 400 is shown alone in FIG. 8. An exemplary leaflet 216 of the valvular structure 204 is shown in a flat (unfolded) configuration in FIG. 10 and an exemplary, folded configuration in FIG. 11. The folded configuration of the leaflet 216 shown in FIG. 11 can represent a form of the leaflet when attached to the frame 202, as described further below. An outer surface 482 of the leaflet 216, which faces the frame 202 after assembly to the frame 202, is shown in FIG. 11.

Each leaflet 216 can have a lower or cusp edge portion 416 (FIG. 10) that can be mounted to the frame 202 by a connecting skirt 410, as described further herein. During assembly to the frame 202, as described in further detail below, the lower cusp edge portion 416 can become folded toward the frame 202, as shown in FIGS. 11 and 12.

Figure 10:
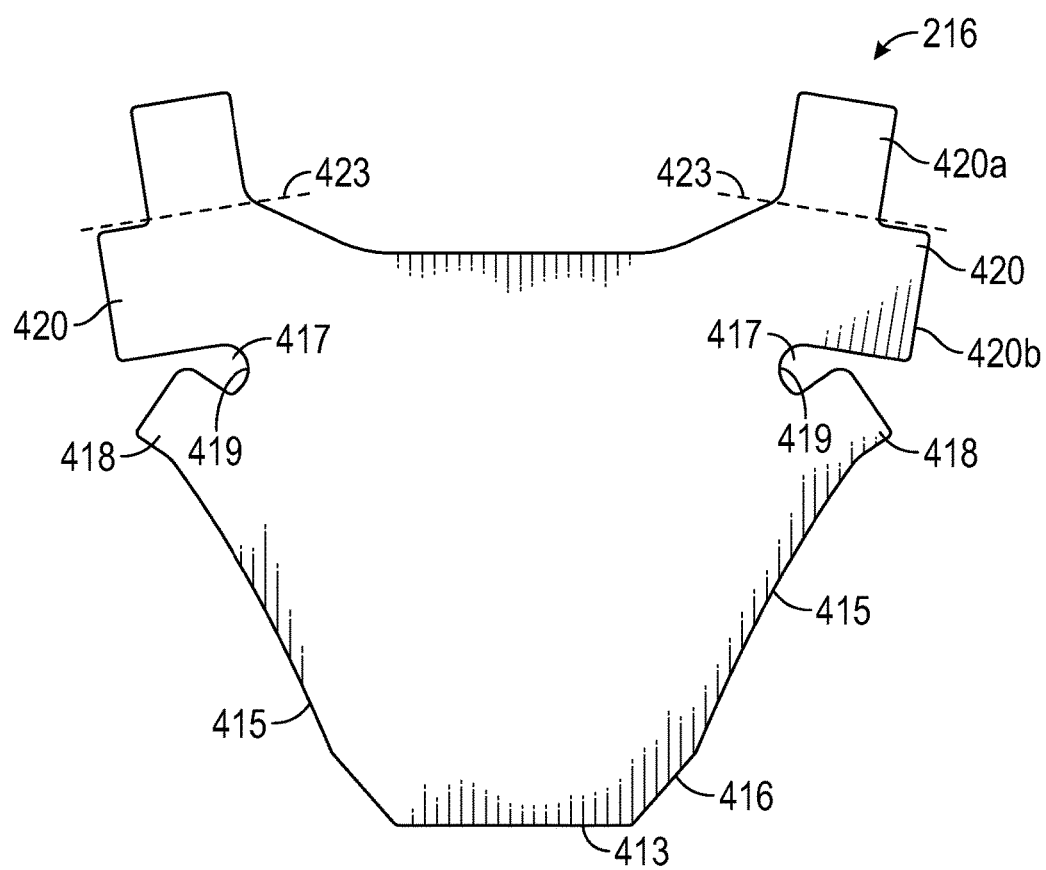
FIG. 10 is a plan view of an example of a leaflet of the prosthetic heart valve of FIG. 7.

As shown in FIG. 10, the cusp edge portion 416 terminates at its upper ends at two laterally projecting integral lower tabs 418. As shown in FIG. 11, during assembly to the frame 12, the lower tabs 418 can fold over onto the outer surface 482. Projecting from the upper corners of the leaflet 216 are integral upper tabs 420 (also referred to as commissure tabs). The upper tabs 420 can be spaced from the lower tabs 818 by side edges 419 forming laterally extending gaps or recesses 417 in the leaflet 216. As described further below and shown in FIG. 11, the upper tabs 420 can be folded over on themselves to form commissures.

Figure 11:
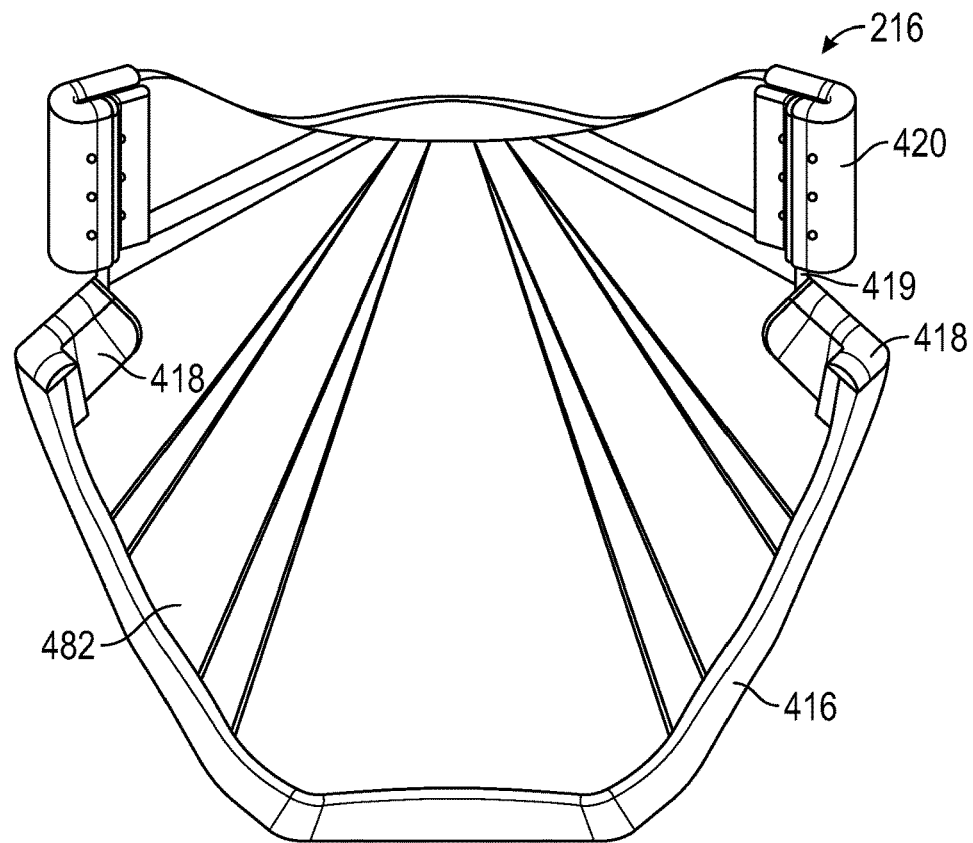
FIG. 11 is a perspective view of the leaflet of FIG. 10 in a folded configuration.
Figure 12:
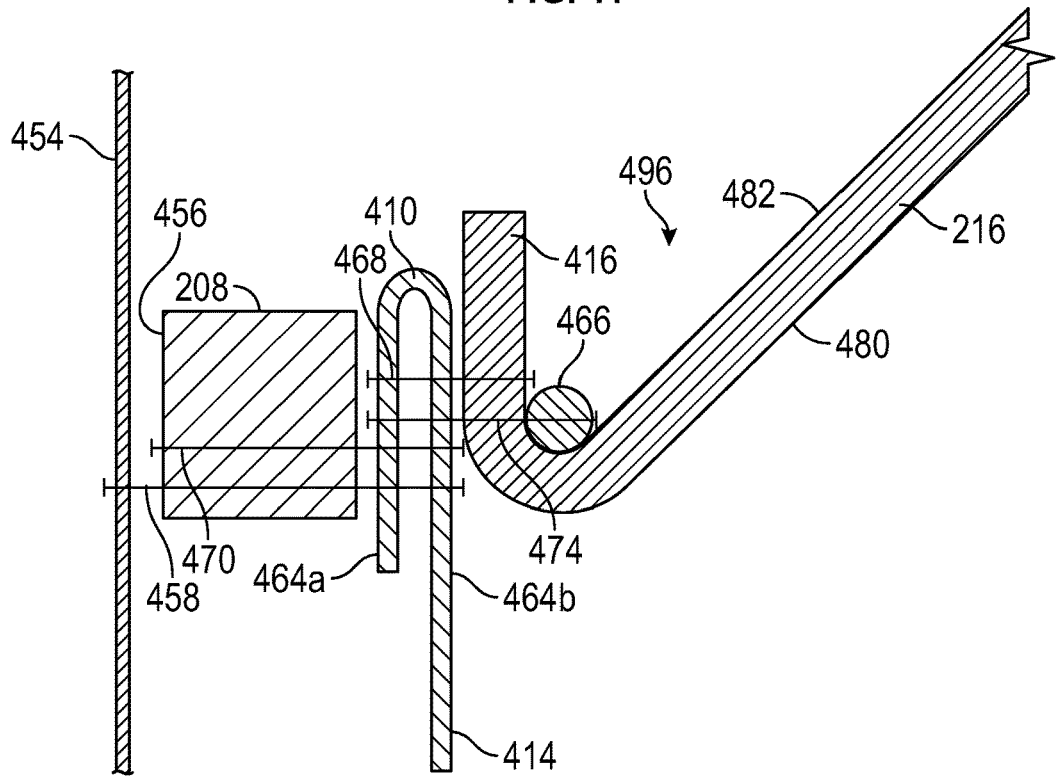
FIG. 12 is a cross-sectional view of the prosthetic valve of FIG. 7 showing an exemplary attachment of the cusp edge portion of a leaflet to the frame via the connecting skirt of FIG. 9.

In alternate examples, the leaflets of the valvular structure 204 can be configured differently that those shown in FIGS. 10 and 11, such as having differently shaped upper tabs or differently sized recesses 417.

Figure 7:
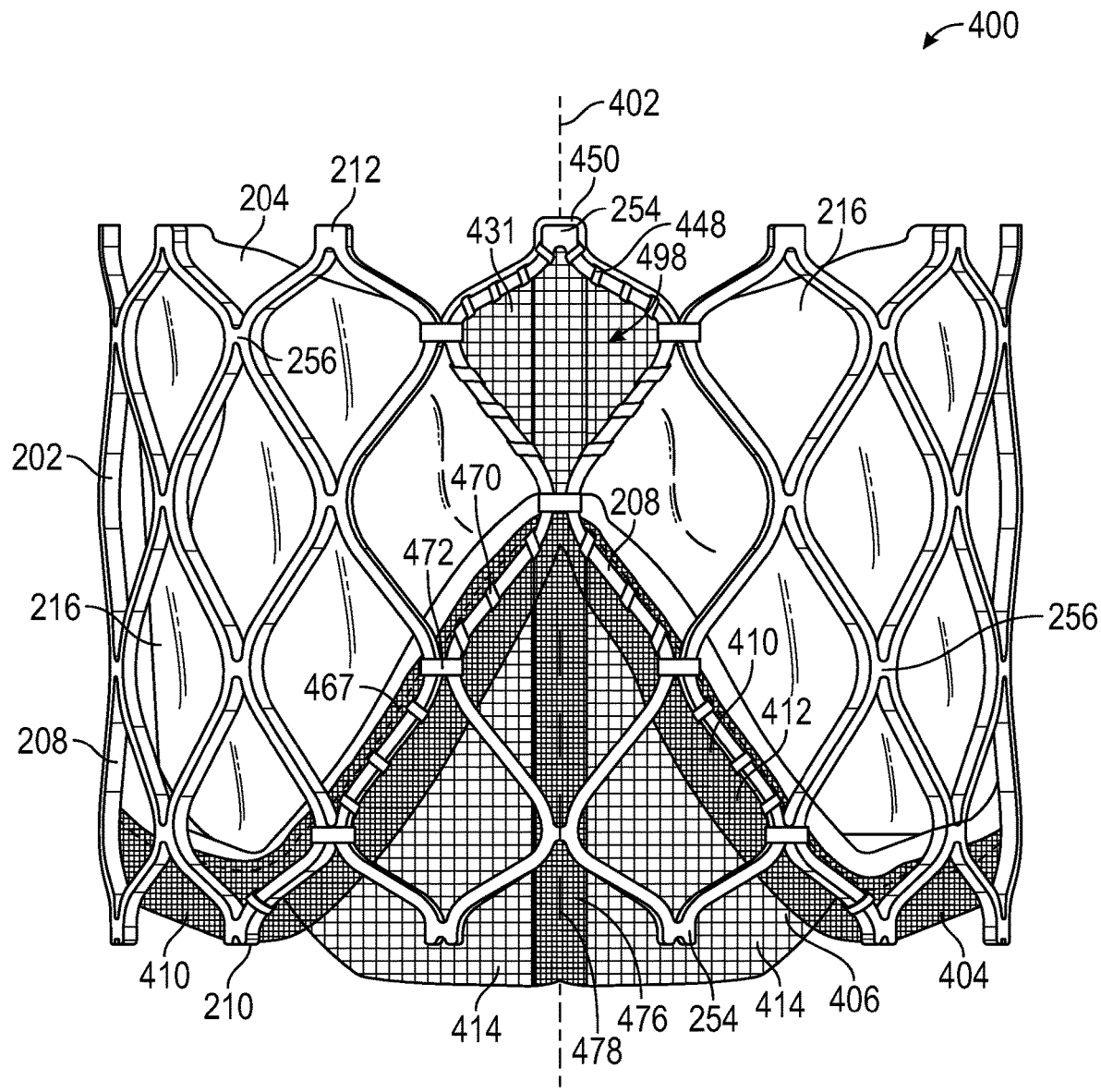
FIG. 7 is a side view of a prosthetic heart valve with components on an outside of a frame of the prosthetic heart valve removed, according to another example, which includes a connecting skirt coupling a cusp edge portion of a leaflet to the frame of the prosthetic heart valve, the connecting skirt including side extension portions that cover apices at an inflow end of the frame.

As shown in FIG. 7, the prosthetic heart valve 400 includes a plurality of connecting skirts (e.g., members) 410 which connect the cusp edge portions 416 of the leaflets 216 to the frame 202 (e.g., in place of connecting skirts 260). For example, each connecting skirt 410 can secure the cusp edge portion 416 of one leaflet 216 to the frame 202. Thus, in the illustrated example, there are a plurality of discrete connecting skirts 410 (one for each leaflet 216) formed from separate pieces of material (e.g., separate pieces of fabric). In alternative examples, the prosthetic valve can have a single connecting skirt that is used for connecting all of the leaflets to the frame. The single connecting skirt can have different sections that are aligned along the cusp edge portions 416 of the leaflets 216.

The connecting skirts 410 include side portions 406 with extension portions 414 that cover the inner surface of the struts 208 (including apices 254) between adjacent leaflets 216, at the inflow end 210 of the frame 202 (FIG. 7). As a result, the inner surface of the apices 254 and struts 208 at the inflow end 210 of the frame 202 are covered and the connecting skirts 410 can serve as a barrier between the apices 254 and struts 208 and the balloon 318 when the prosthetic heart valve is radially compressed onto and around the balloon 318 (as described further below with reference to FIG. 26).

Figure 9:
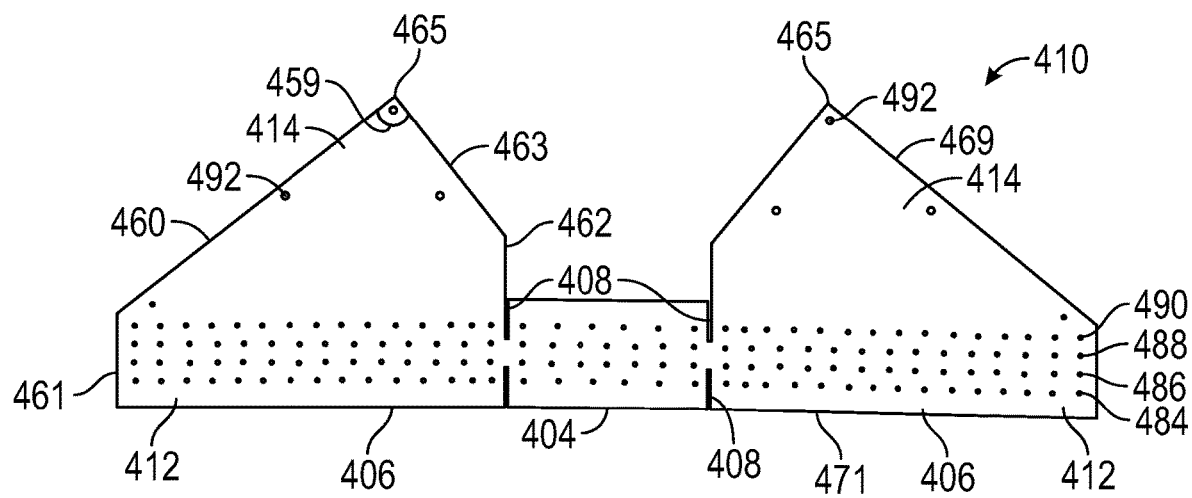
FIG. 9 is a plan view of an example of a connecting skirt for connecting a cusp edge portion of a leaflet to the frame of the prosthetic heart valve of FIG. 7.

A single connecting skirt 410 of the prosthetic heart valve 400 is shown in FIG. 9. In some examples, the connecting skirt 410 can comprise a synthetic material, such as fabric (e.g., PET fabric), or a natural tissue material (e.g., pericardial tissue). In the illustrated example, a single connecting skirt 410 is provided for a cusp edge portion 416 of each leaflet 216 and is sized to extend along the entire length of the cusp edge portion 416 to locations just below lower tabs 418 of the leaflet 216 (FIG. 10).

Figure 14:
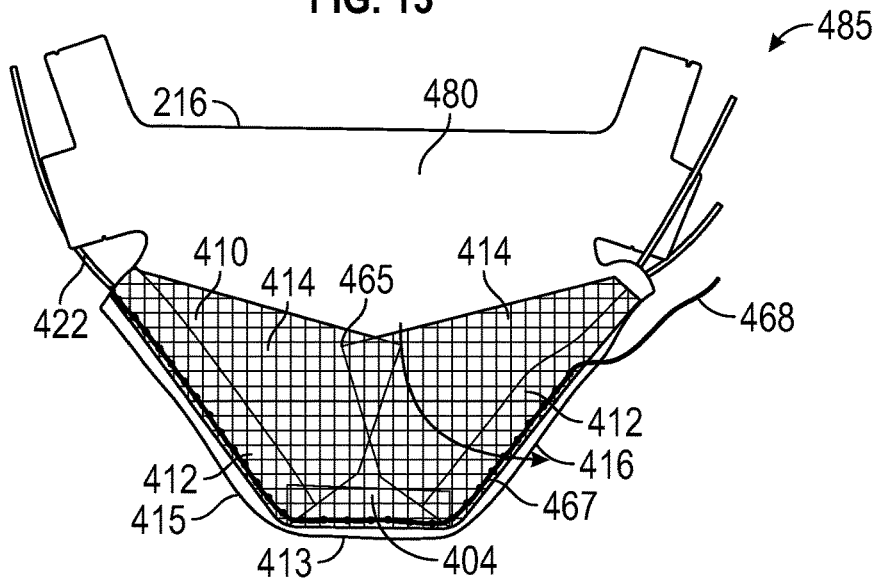
FIG. 14 is a plan view of an inner surface of the leaflet of FIG. 10 illustrating the connecting skirt of FIG. 9 placed along and attached to the inner surface of the cusp edge portion of the leaflet.

FIG. 14 shows a connecting skirt 410 placed along an inner surface 480 of the cusp edge portion 416 of a leaflet 216 and attached to the cusp edge portion 416 of the leaflet 216. As shown in FIG. 9, the connecting skirt 410 can include a central portion 404 sized to extend over a central portion 413 of the cusp edge portion 416 of the leaflet 216 (e.g., central cusp edge portion 413) and two side portions 406 sized to extend over corresponding angled side edge portions 415 of the cusp edge portion 416 of the leaflet 216. As shown in FIG. 10, each angled side edge portion 415 can extend from the central portion 413 to a respective one of the lower tabs 418 of the leaflet 216.

Each side portion 406 of the connecting skirt 410 can include a base portion 412 (also referred to as a side base portion) and an extension portion 414 (also referred to as a side extension portion) which extends outwardly from the base portion 412. In some examples, as shown in FIG. 9, each extension portion 414 of the corresponding side portion 406 can be triangular. In some examples, the base portions 412 and the central portion 404 can be rectangular.

For example, each extension portion 414 can include a first angled edge 460 that extends outward, at an angle, from and relative to a free end 461 of the base portion 412 of the corresponding side portion 406. Each extension portion 414 can further include a perpendicular edge 462 that extends outward from an end of the base portion 412 that is connected to the central portion 404 of the connecting skirt 410. The perpendicular edge 462 can be parallel to the free end 461 of the base portion 412 of the corresponding side portion 406. The extension portion 414 can further include a second angled edge 463 that extends outward (e.g., away from the base portion 412), at an angle, from and relative to the perpendicular edge 462. The first angled edge 460 and the second angled edge 463 can meet at a point 465 that is spaced outward and away from the base portion 412. Thus, extension portions 414 of the side portions 406 extend outward and past the central portion 404 of the connecting skirt 410.

In some examples, an angle 459 between the first angled edge 460 and the second angled edge 463 can be in a range of about 45 degrees to about 120 degrees, about 75 degrees to about 100 degrees, or about 85 degrees to about 95 degrees.

Thus, due to the shape of the side portions 406 of the connecting skirt 410, the connecting skirt 410 can have a relatively straight first edge 471 (e.g., bottom edge in FIG. 9) extending across the central portion 404 and the two side base portions 412 and a non-straight second edge 469 (e.g., top edge in FIG. 9) extending from the free end 461 of one of the base portion 412 of the side portions 406 to the free end 461 of the other one of the base portions 412 of the side portions 406. The first edge 471 and the second edge 469 can be arranged opposite one another across the connecting skirt 410. Further, the second edge 469 can comprise multiple differently angled edges.

In some examples, together, the central portion 404 and the two base portions 412 can be referred to as a base portion of the connecting skirt and the two extension portions 414 can extend outwardly and away from the base portion.

The connecting skirt 410 can be formed with slits 408 partially separating the side portions 406 from the central portion 404 (FIG. 9) to facilitate alignment of the connecting skirt 410 along the cusp edge portion 416 of the leaflet 216, as shown in FIG. 14. For example, the slits 408 can be configured to allow the base portions 412 of the side portions 406 to bend (e.g., at an angle) relative to the central portion 404.

In alternative examples, plural connecting skirts can be provided for the cusp edge portion 416 of each leaflet 216 (e.g., the central portion 404 and the side portions 406 can be separate pieces of fabric). In another example, a single connecting skirt can be used to secure all of the leaflets 216 to the frame 202 (e.g., a single connecting skirt can be sized to extend along the cusp edge portions 416 of all of the leaflets 216 of the valvular structure 204).

Figure 13:
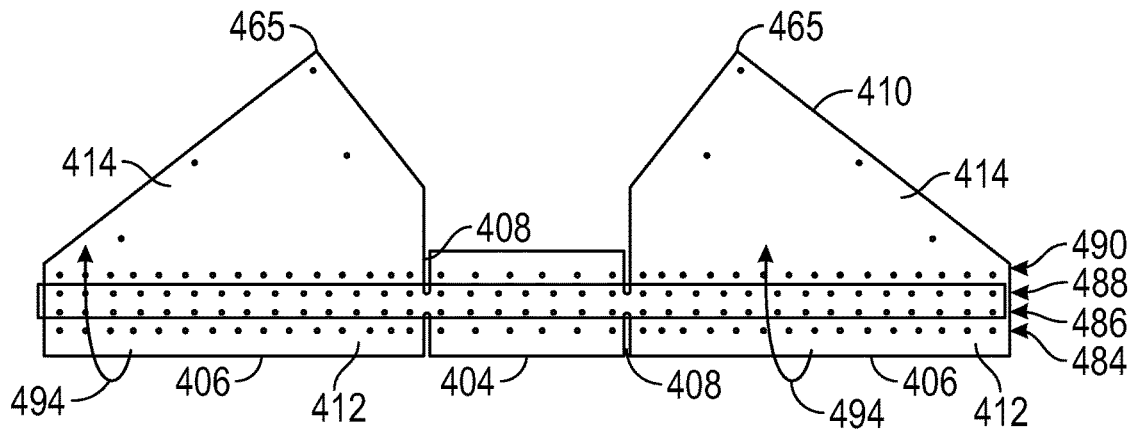
FIG. 13 is a plan view of the connecting skirt of FIG. 9 illustrating a folding method for securing the connecting skirt to a leaflet.

In some examples, each connecting skirt 410 can include a plurality of apertures configured as suture holes that are configured to receive a stitch or suture for attaching the connecting skirt 410 to the leaflet 216 and/or the frame 202. For example, in some examples, the apertures can include a first row of apertures 484, a second row of apertures 486, a third row of apertures 488, and a fourth row of apertures 490 which each include a plurality of apertures spaced apart from one another along a length of the base portion 412 of each side portion 406 and the central portion 404 (FIGS. 9 and 13). In some examples, each extension portion 414 of the connecting skirt 410 can also include one or more apertures 492 (FIG. 9) that can be used to secure each extension portion 414 to another extension portion 414 of an adjacent connecting skirt 410 (e.g., as shown in FIG. 7). In some examples, the one or more apertures 492 are disposed in the extension portion, adjacent to (e.g., spaced apart along) the first angled edge 460.

Figure 22:
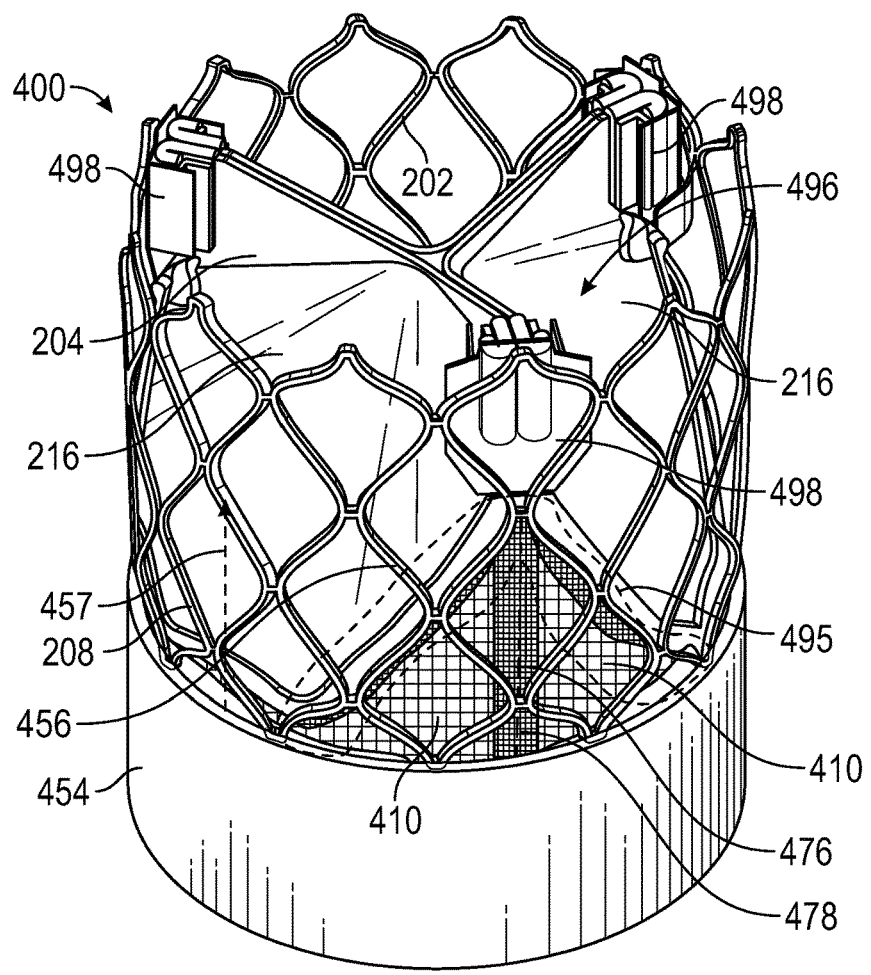
FIG. 22 is a perspective view of the prosthetic heart valve of FIG. 7 illustrating a method for securing an outer sealing member to an outer surface of the struts of the frame of the prosthetic heart valve.
Figure 25:
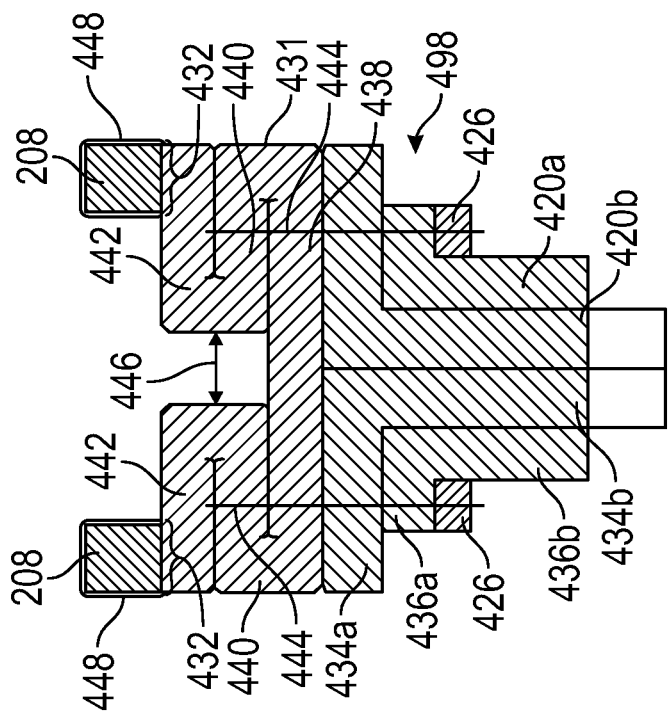
FIG. 25 is a cross-sectional view of one of the commissures of the prosthetic heart valve of FIG. 7, the commissure including the commissure attachment member of FIG. 23.
Figure 23:
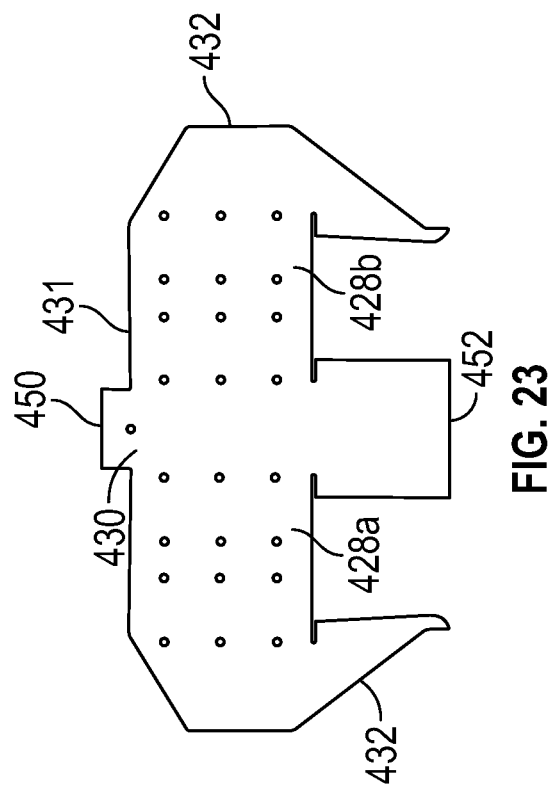
FIG. 23 is a plan view of an example of a commissure attachment member, shown in a flattened configuration.
Figure 24:
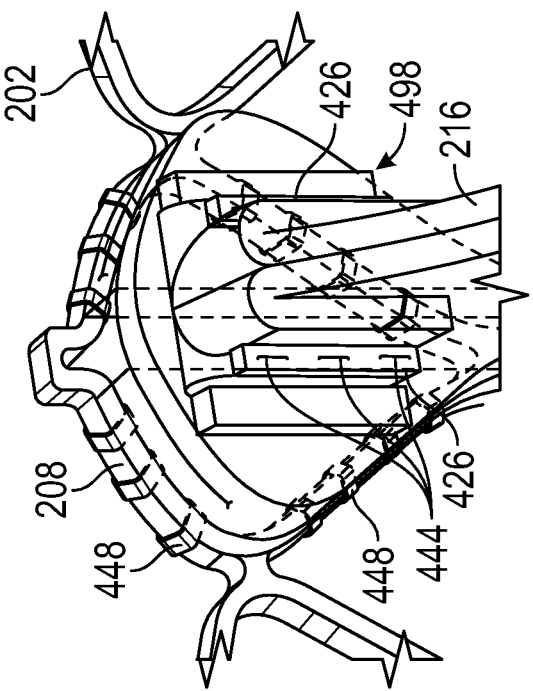
FIG. 24 is a perspective view of one of the commissures of the prosthetic heart valve of FIG. 7, the commissure including the commissure attachment member of FIG. 23.
Figure 26:
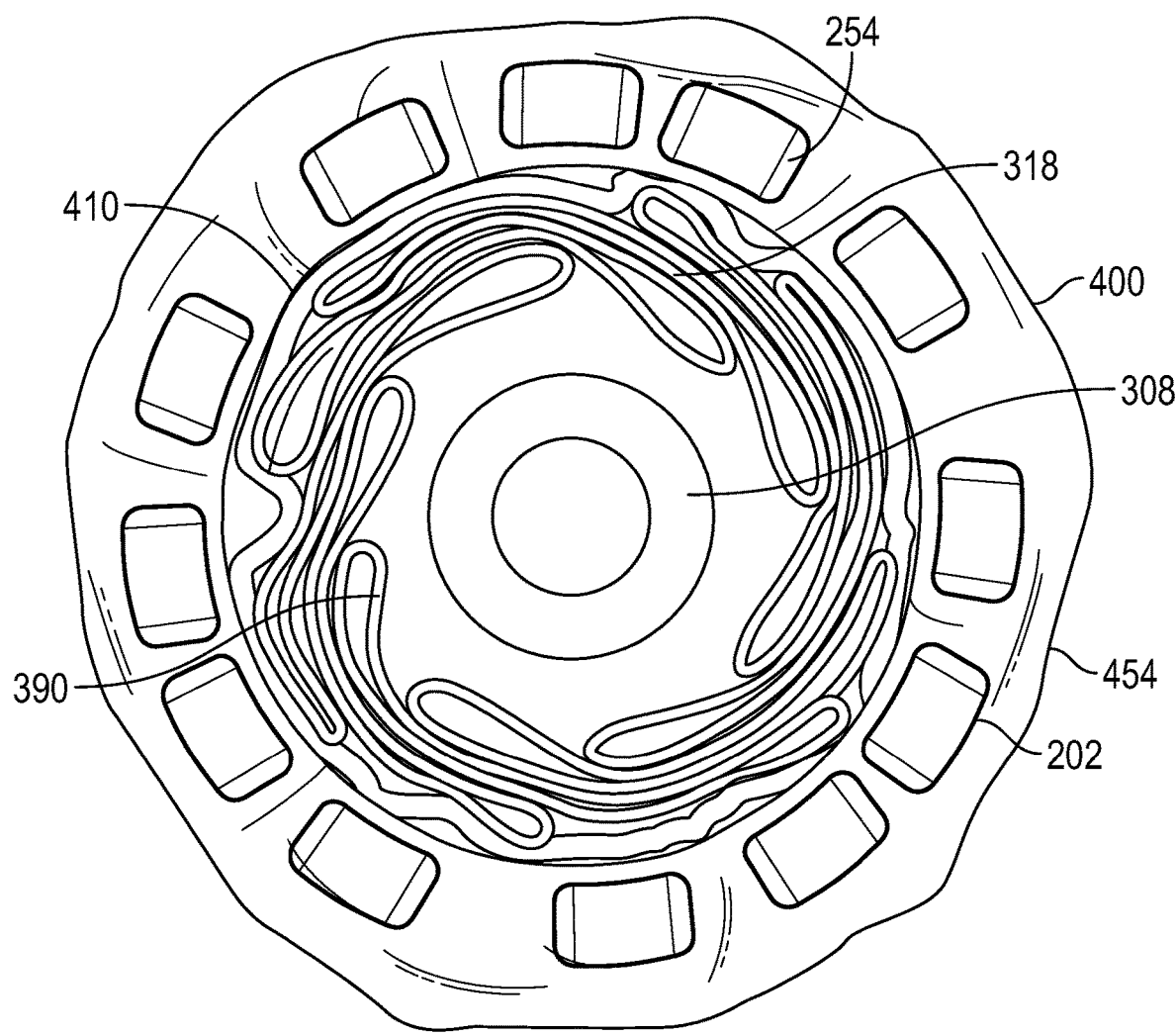
FIG. 26 is a cross-sectional view of the prosthetic heart valve of FIG. 7 radially compressed onto and around an inflatable balloon of a delivery apparatus.

FIGS. 12-25 show assemblies and methods for assembling the valvular structure 204 to the frame 202, including methods for attaching the connecting skirts 410 to their respective leaflets 216 (FIGS. 13-16), methods for forming the valvular structure 204 (FIG. 17), methods for attaching the connecting skirts 410 to the frame 202 (FIGS. 19-21), and methods for forming commissures and attaching the commissures to the frame 202 (FIGS. 23-25).

To attach a connecting skirt 410 to a corresponding leaflet 216, the base portions 412 of the side portions 406 and the central portion 404 can first be folded over on themselves (e.g. in half), as illustrated by the arrows 494 in FIG. 13. For example, as shown in the cross-sectional view of FIG. 12, folding the base portions 412 and the central portion 404 lengthwise (as shown in FIG. 13) can form two fold layers 464a, 464b, with the extension portions 414 extending outward from one of the two fold layers (e.g., fold layer 464b in FIG. 12).

The folded base portions 412 and central portion 404 can then be arranged along the inner surface 480 of the cusp edge portion 416 of the leaflet 216 (FIG. 14). For example, as introduced above and as shown in FIG. 14, the folded central portion 404 can be positioned over the central portion 413 of the cusp edge portion 416 of the leaflet 216 and each base portion 412 can be positioned over a corresponding angled side edge portion 415 of the cusp edge portion 416 of the leaflet 216.

As shown in FIG. 14, in some examples, adjacent portions of the central portion 404 and each of the base portions 412 can overlap in a region of the slits 408 due to the bending of the base portions 412 relative to the central portion 404, which is facilitated by the slits 408.

The extension portions 414 of the side portions 406 of the connecting skirt 410 extend away from the cusp edge portion 416 and across a portion of the inner surface 480 of the leaflet 216. In some examples, as shown in FIG. 14, the two extension portions 414 of the connecting skirt 410 overlap one another in a region of their points 465.

After placing the connecting skirt 410 on the inner surface 480 of the leaflet 216, as shown in FIG. 14, the folded base portions 412 and central portion 404 can be secured to the cusp edge portion 416. For example, the folded base portions 412 and central portion 404 can be secured to the cusp edge portion 416 via one or more sutures (e.g., stitching) 468 that form a stitching line 467 along the cusp edge portion 416 (FIGS. 12 and 14). In some examples, the stitching line 467 can comprise a plurality of in and out stitches that extend through the cusp edge portion 416 of the leaflet 216 and overlapping apertures of the second row of apertures 484 and the third row of apertures 488 of the connecting skirt 410. For example, when the base portions 412 and the central portion 404 of the connecting skirt 410 are folded as described above and shown in FIG. 14, the two middle rows of apertures (e.g., the second row of apertures 486 and the third row of apertures 488 shown in FIG. 13) can overlap one another, thereby forming a single row of double-layered apertures configured to receive the in and out stitches of the one or more sutures 468.

Figure 15:
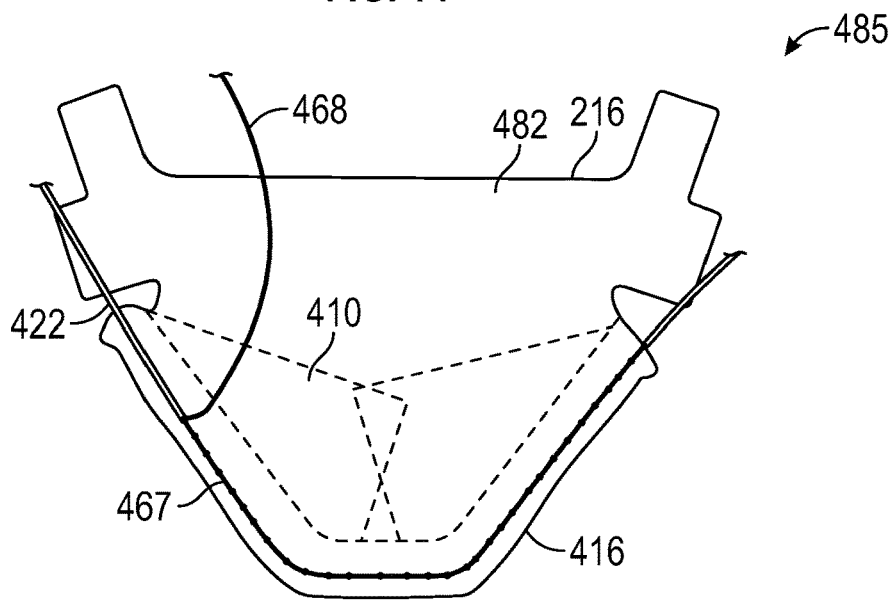
FIG. 15 is a plan view of an outer surface of the leaflet of FIG. 10 illustrating the connecting skirt of FIG. 9 attached to the cusp edge portion of the leaflet.

While FIG. 14 shows the inner surface 480 of the leaflet 216, FIG. 15 shows the opposite, outer surface 482 of the leaflet 216. Since the connecting skirt 410 is behind the leaflet 216 in the view of FIG. 14, the edges of the connecting skirt 410 are illustrated with dashed lines. The stitching line 467 formed by the one or more sutures 468 can be seen on the outer surface 482 of the leaflet 216 (FIG. 15).

Together, the leaflet 216 and attached connecting skirt 410, as shown in FIGS. 14 and 15, can form and be referred to herein as a leaflet assembly 485.

Figure 16:
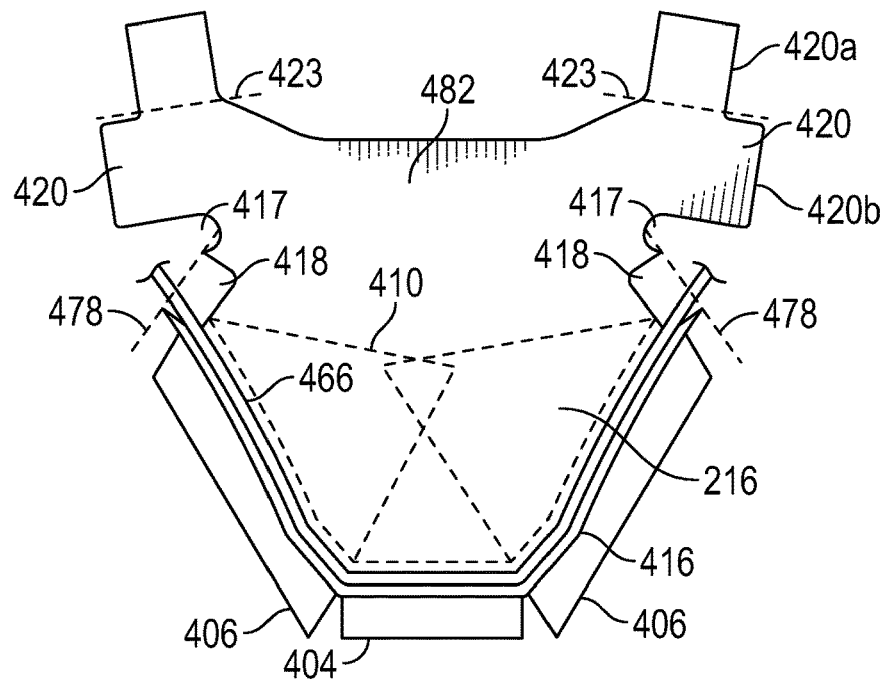
FIG. 16 is a plan view of the leaflet of FIG. 10 including the connecting skirt of FIG. 9 and a reinforcing member positioned along the cusp edge portion of the leaflet.

In some examples, a reinforcing member or chord 466 (e.g., an Ethibond suture) can be placed against the outer surface 482 of the cusp edge portion 416, opposite the connecting skirt 410 (FIG. 16). The reinforcing chord 466 and the fold layers 464a, 464b can be sutured to each other and to the cusp edge portion 416 with stitching 474, which can be a single suture or multiple sutures extending through one or more layers of material (FIG. 12).

In some examples, when suturing the reinforcing chord 466 to the leaflet 216, the lower tabs 418 can be folded downwardly against the cusp edge portion 416 (see FIG. 16) and the reinforcing chord 466 can be placed over the folded lower tab 418. The upper ends of the connecting skirt 410 can be sized to extend over the folded lower tabs 418. Stitching 474 can be used to secure the reinforcing chord 466 in place against the folded lower tab 418 (FIG. 12).

In some examples, a single reinforcing chord 466 can extend continuously along the cusp edge portions 416 of all of the leaflets 216 of the valvular structure 204 and through the spaces beneath each commissure 498. In other examples, plural reinforcing chords 466 can be used, with one reinforcing chord secured to the cusp edge portion of each leaflet 216. Where multiple reinforcing chords 466 are used, the ends of each chord can be connected (e.g., by tying or knotting) to adjacent ends of the other chords. For example, adjacent ends of two chords can be connected to each in the space underneath a commissure.

Figure 17:
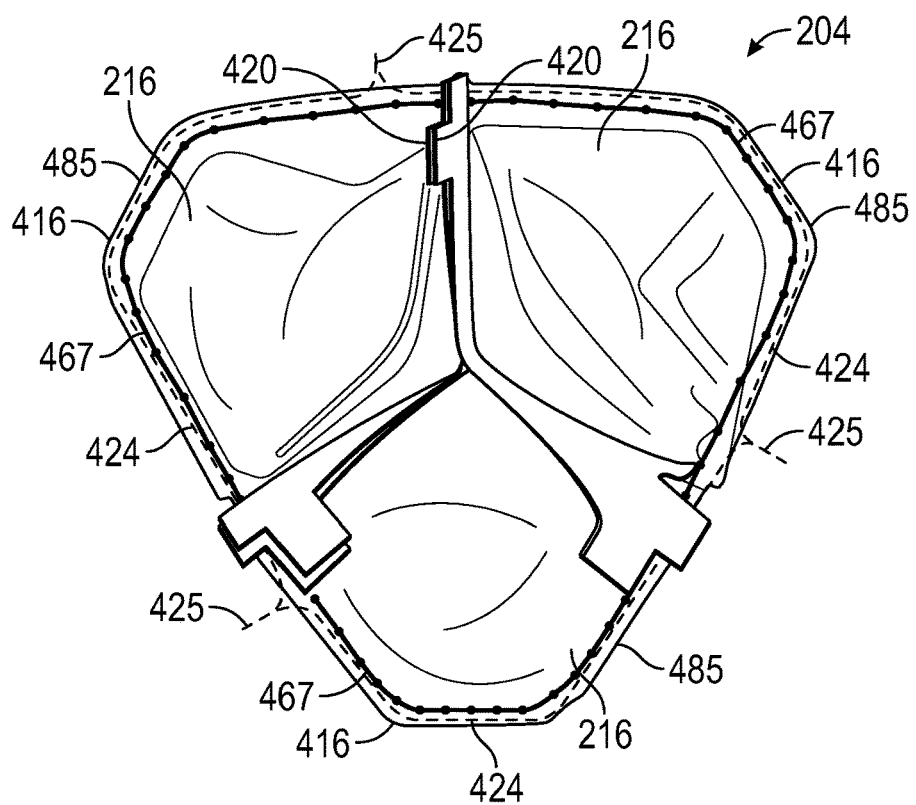
FIG. 17 is a plan view of a plurality of leaflets and connecting skirts secured together to form a valvular structure for the prosthetic heart valve of FIG. 7.

After each connecting skirt 410 is secured to each respective leaflet 216, forming a leaflet assembly 485, the leaflet assemblies 485 (e.g., three shown in FIG. 17) can be secured together to form the valvular structure 204, as shown in FIG. 17. Though the valvular structure 204 comprises three leaflets 216 and leaflet assemblies 285, in alternate examples, a leaflet structure for the prosthetic valves discussed herein can have a different number of leaflets, such as two leaflets.

As shown in FIG. 17, the three leaflet assemblies 485 are arranged together, in a flat configuration, with the cusp edge portions 416 of the leaflets 216 forming an outer perimeter of the valvular structure 204 and with upper tabs 420 from adjacent leaflets 216 folded upward and positioned against one another. The three leaflet assemblies 485 can be secured (e.g., sutured or otherwise fastened) together via one or more sutures 422 (FIGS. 14 and 15) that form a stitching line 424 along and between each of the cusp edge portions 416 of each leaflet 216 (FIG. 17).

In some examples, one or more tails 425 of the one or more sutures 422 can be connected to struts 208 of the frame 202.

Once the leaflet assemblies 485 are secured together, the valvular structure 204 can be arranged within an interior of the frame 202 and secured to the frame 202, as shown in FIGS. 7, 12, and 19-24.

To secure the cusp edge portions 416 of each leaflet 216 of the valvular structure 204 to the frame 202, the folded over central portion 404 and base portions 412 of each connecting skirt 410 can be secured (e.g., sutured) to struts 208 of the frame 202. In some examples, one or more sutures 470 (forming stitches) can extend through the folded over central portion 404 and base portions 412 of each connecting skirt 410 and around struts 208 of the frame 202, along a length of the cusp edge portions 416 to secure the cusp edge portions 416 of the leaflets 216 to the frame 202 (FIGS. 19 and 20).

Figure 19:
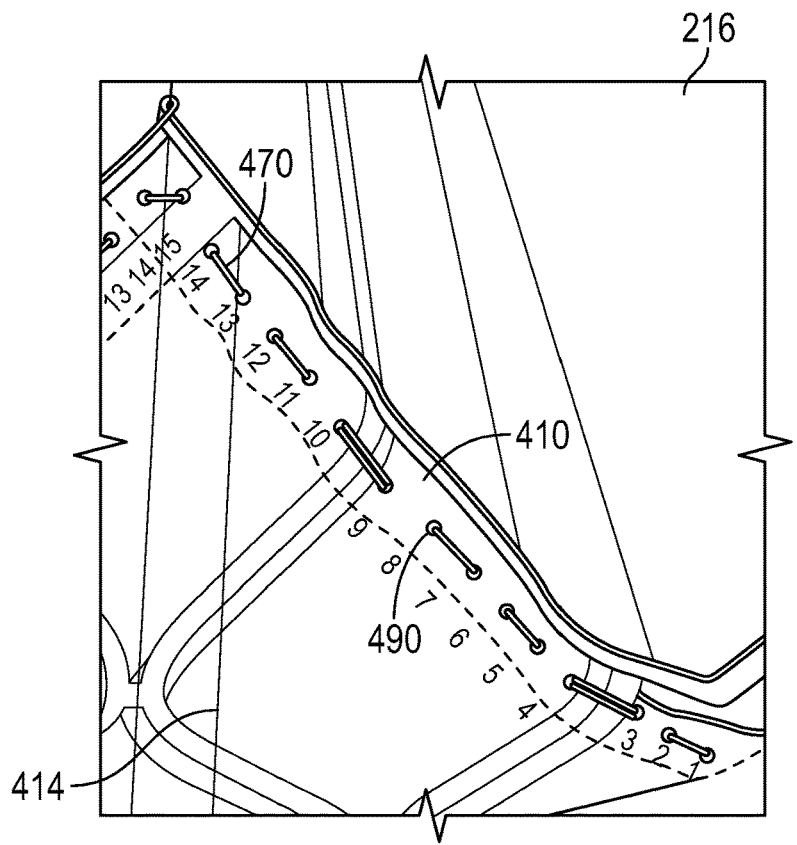
FIG. 19 is a detail view of the connecting skirt of FIG. 9 secured to struts of the frame of FIG. 8 from the perspective of an interior of the frame.
Figure 20:
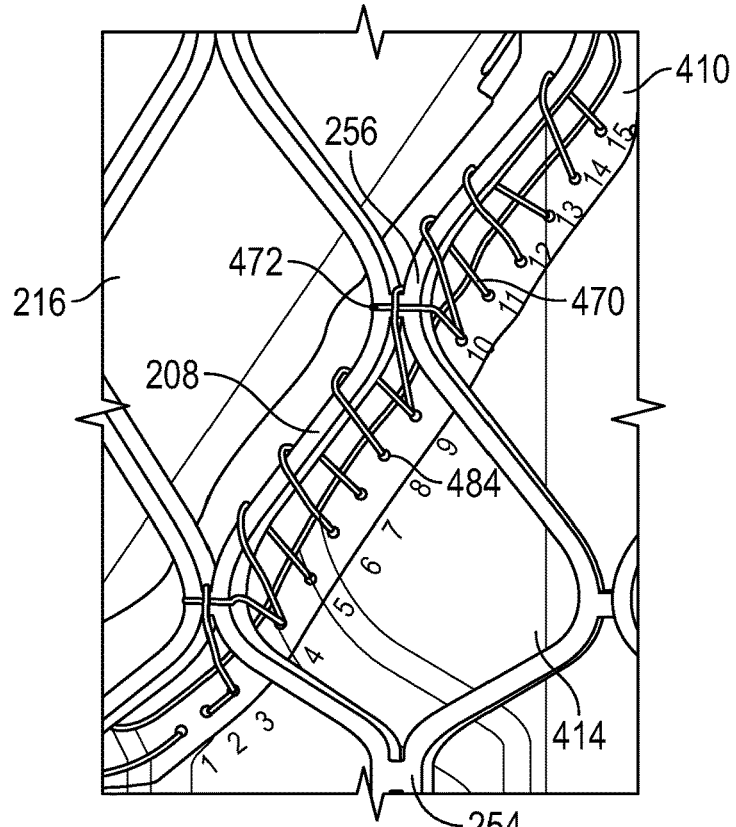
FIG. 20 is a detail view of the connecting skirt of FIG. 9 secured to struts of the frame of FIG. 8 from the perspective of an exterior of the frame.

For example, FIGS. 19 and 20 show detail views of the one or more sutures 470 securing the connecting skirts 410 to the struts 208 of the frame 202 from the perspective of an interior of the frame 202 (FIG. 19) and an exterior of the frame 202 (FIG. 20). As explained above, when the central portion 404 and base portions 412 of each connecting skirt 410 are folded over, as shown in FIGS. 19 and 20, the first row of apertures 484 and the fourth row of apertures 490 (FIGS. 9 and 13) of the connecting skirt 410 can overlap one another and form a single row of apertures configured to receive the stitches of the one or more sutures 470 (FIGS. 19 and 20). The overlapping apertures are numbered in FIGS. 19 and 20 to show a correspondence between the inner surface (FIG. 19) and the outer surface (FIG. 20) of the connecting skirt 410.

In some examples, the one or more sutures 470 can extend through the folded over portions of the connecting skirt 410, around a strut 208 (as shown from the exterior view of FIG. 20), and then back through the connecting skirt 410 to an interior surface of the frame 202 (as shown in FIG. 19). These stitches can repeat along a length of the central portion 404 and base portions 412 of each connecting skirt 410 (e.g., along the cusp edge portions 416 of the leaflets 216), thereby connecting each connecting skirt 410 to a first set or portion of struts 208 that extend at an angle from a first commissure 498 to the inflow end 210 and from the inflow end to a second commissure 498 (FIGS. 7 and 22).

In some examples, the stitches formed by the one or more sutures 470 can comprise a plurality of whip stitches. In some examples, individual stitches 472 can secure each connecting skirt 410 to corresponding strut junctions 256 (FIGS. 7 and 20). Thus, in some examples, the two fold layers 464a and 464b of each connecting skirt 41 can be secured to strut junctions 256 by individual stitches 472 and whip stiches of the one or more sutures 470 that are formed along the length of a struts 208 between two strut junctions 256, as shown in FIGS. 7 and 12.

In some examples, the whip stitches of the one or more sutures 470 optionally can extend through the cusp edge portion 416 of the leaflets 216.

Figure 18:
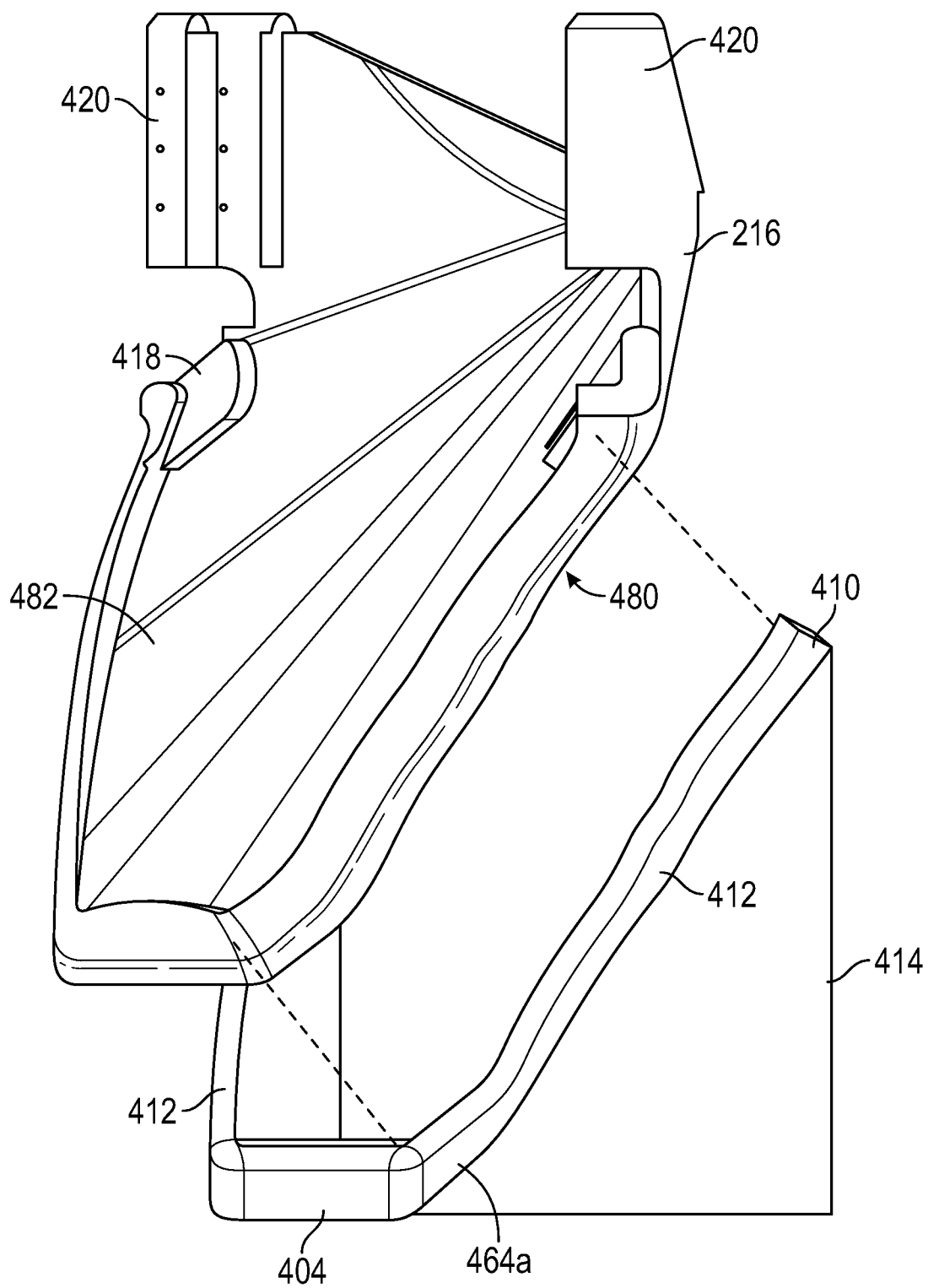
FIG. 18 is an exploded, perspective view of the leaflet of FIG. 10 and the connecting skirt of FIG. 9 in a configuration for attachment to the frame of FIG. 8.

In some examples, attaching the connecting skirt 410 to the frame 202, as described above, can cause the cusp edge portion 416 of the leaflet 216 to fold over itself, toward the frame 202, as shown in FIGS. 11, 12, and 18. As a result, the inner surface 480 of the cusp edge portion 416 now faces an inner surface of the frame 202. Further, as a result of this folding, the fold layer 464a of the connecting skirt 410 faces the inner surface of the frame 202 (FIGS. 12 and 18) and the extension portions 414 of the connecting skirt 410 are folded away from the inner surface 480 of the leaflet 216 and toward the inner surface of the frame 202 (FIGS. 12 and 18). For example, FIG. 18 is an exploded, perspective view of a leaflet 216 and a connecting skirt 410, as they would appear when attached to the frame 202.

As a result of the folding over of the cusp edge portion 416 of the leaflet 216 as it is attached to the frame 202, the extension portions 414 can cover a second set or portion of struts 208 and apices 254 of the frame 202 that are arranged at the inflow end 210, between cusp edge portions 416 of adjacent leaflets 216 (FIGS. 7, 19, and 20).

Figure 21:
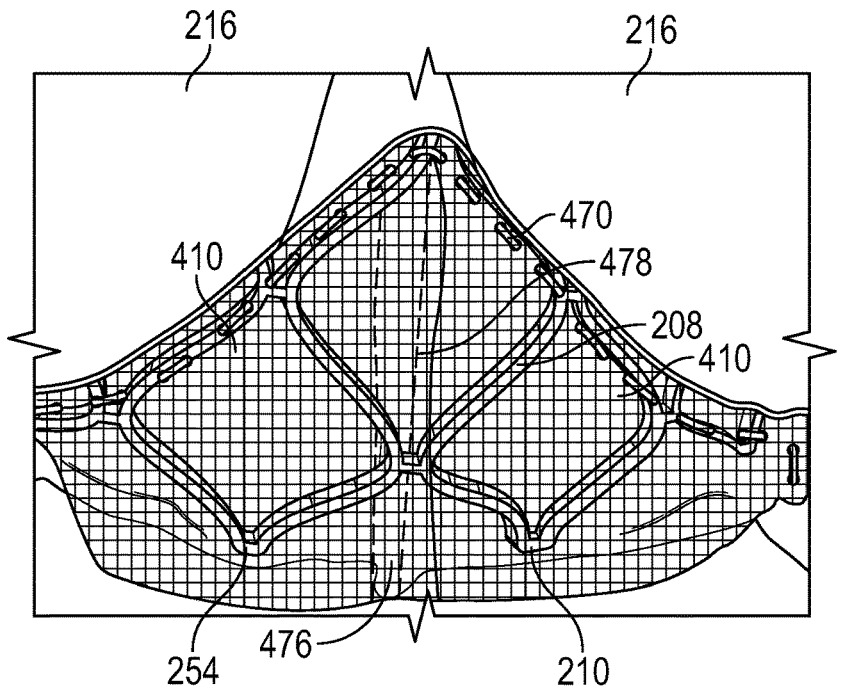
FIG. 21 is a perspective, detail view from an inside of the prosthetic heart valve of FIG. 7 illustrating inner surfaces of two extension portions of two adjacent connecting skirts and a connection between the two extension portions.

In some examples, portions of two adjacent extension portions 414 of two adjacent connecting skirts 410 overlap one another, thereby forming overlapping extension portions 476. As shown in FIGS. 7, 21, and 22, in some examples, the overlapping extension portions 476 can be secured together via one or more sutures 478 (or other similar fasteners or fastening members), thereby securing two extension portions 414 of two adjacent connecting skirts 410 to one another. In some examples, the extension portions 476 can be secured to struts of the frame 202, such as a strut junction 256 which the extension portions 476 overlay, by the sutures 478 or by additional sutures.

FIG. 21 is a perspective, detail view of inner surfaces of the extension portions 414 of two adjacent connecting skirts 410 and the inner surfaces 480 of two adjacent leaflets 216 (e.g., from the inside of the valve and frame 202). In contrast, FIGS. 7 and 22 show an exterior view of the prosthetic heart valve 400 and outer surfaces of the extension portions 414 of the connecting skirts 410.

As shown in FIG. 21, the extension portions 414 of the connecting skirts 410 extend over and cover the inner surfaces of the struts 208 and apices 254 arranged between adjacent leaflets 216 at the inflow end 210 of the frame 202. As a result, the connecting skirts 410 are disposed between the frame 202 and an interior 496 of the prosthetic heart valve 400 (FIGS. 12 and 22).

Thus, when the prosthetic heart valve 400 is radially compressed around and onto an inflatable balloon of a delivery apparatus (e.g., balloon 318), as shown in FIG. 26, the material of the connecting skirts 410 is positioned between the apices 254 of the frame 202 and the balloon 318, thereby serving as a protective barrier between the struts 208 of the frame 202 and the balloon 318. As a result, degradation to the balloon can be reduced and/or prevented.

The valvular structure 204 can be further secured to the frame 202 by forming commissures 498 and mounting them to the frame 202, as shown in the exemplary method presented at FIGS. 23-35. As introduced above and shown in FIG. 10, each leaflet 216 can include lower tabs 418 and upper tabs 420 (also referred to as commissure tabs). The upper tabs 420 can be spaced from the lower tabs 418 by side edges 419 forming laterally extending gaps or recesses 417 in the leaflet.

As shown in FIGS. 10 and 16, each upper tab 420 can be folded along a fold line 423 to form first and second tab layers 420a and 420b. The upper tab 420 can be secured to a commissure attachment member 431, along with the upper tab 420 of an adjacent leaflet to form a commissure 498, as further described below. FIG. 23 shows a commissure attachment member 431 in a flattened configuration prior to folding and attachment to the leaflets. Each commissure attachment member 431 in the illustrated configuration comprises first and second side portion 428a, 428b projecting laterally from a central portion 430. As shown, the outer peripheral edges 432 of the side portions 428a, 428b can be shaped to correspond to one half of a diamond-shaped cell 214 of the frame 202 to facilitate mounting of the commissure attachment member 431 to the struts 208 of the frame 202, as described further below.

Referring to FIGS. 24 and 25, after the upper tab 420 of a leaflet 216 is folded, a vertical reinforcement 426 can be secured to the inner surface of tab layer 420a, such as with stitching. The folded tab layers 420a, 420b can be secured to a side portion 428a or 428b of the commissure attachment member 431. The folded tab layers 420a, 420b also can be folded along a vertical fold line at the reinforcement 426 in an L-shape such that the tab layer 420b forms a first circumferentially extending layer 434a and a first radially extending layer 434b that is generally perpendicular to the layer 434a and the tab layer 420a forms a second inner circumferentially extending layer 436a and a radially extending layer 436b that is generally perpendicular to the layer 436a. Another upper tab 420 of an adjacent leaflet 216 can be similarly folded and secured to the other side portion 428a or 428b of the commissure attachment member 431.

The commissure attachment member 431 can be folded as shown in FIG. 25 to form an inner layer 438 and two intermediate layers 440 and two outer layers 442. Each folded upper tab 420 can be secured to the inner layer 438 and an intermediate layer 440 with stitching 444. In the illustrated example, stitching 444 is shown extending through the reinforcement member 426, a layer 436a, a layer 434a, a layer 438, and a layer 440. However, during the assembly process, multiple stitches can be employed to secure each layer to an adjacent layer as each folded is created. For example, layers 434a, 436a can be secured to each other and a reinforcement member 426 with separate stitching, and additional stitching can then be used to secure the leaflet layers to the inner layer 438 of the commissure attachment member 431, and further stitching can be used to secure an intermediate layer 440 to the inner layer 438. As best shown in FIG. 25, the commissure attachment member 431 can be folded to leave a small gap 446 between the outer layers 442.

Figure 8:
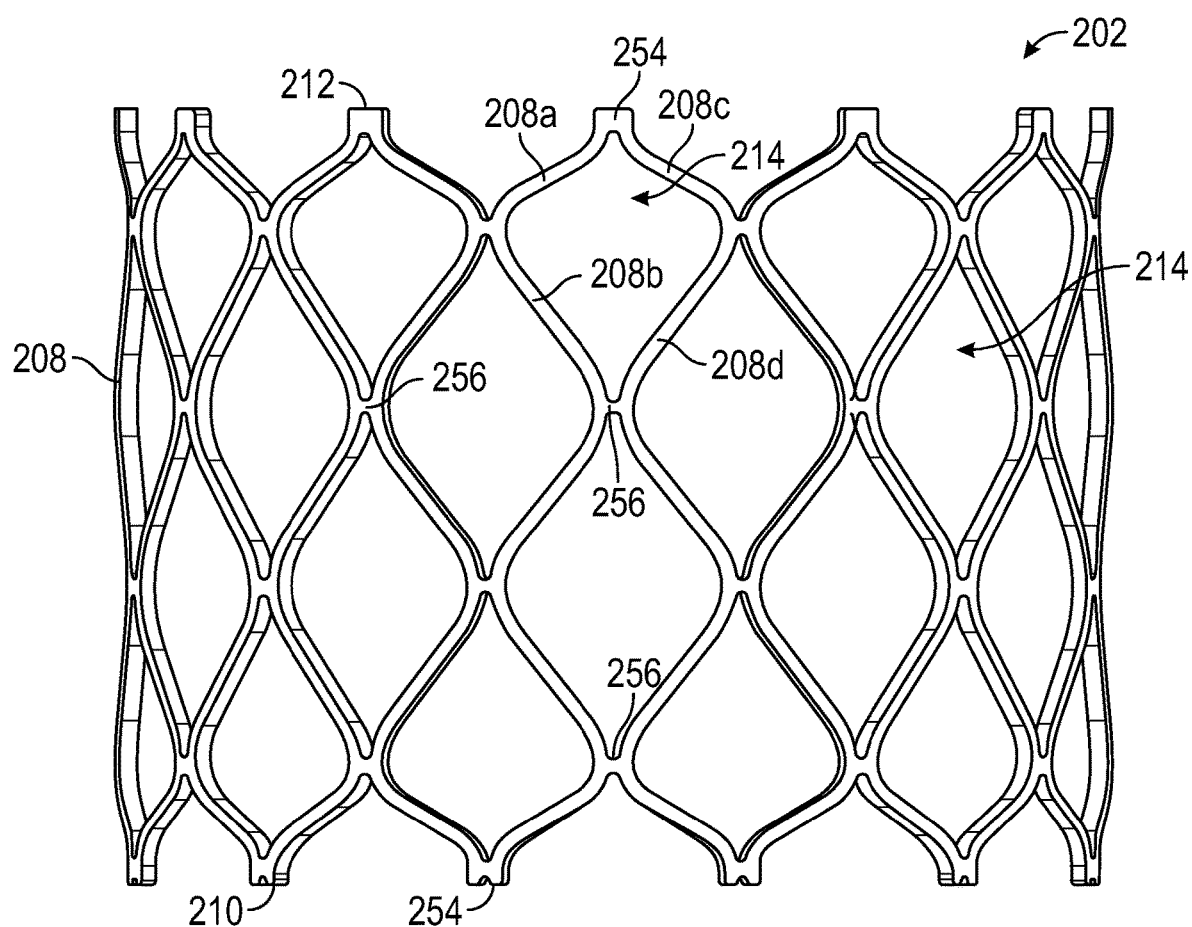
FIG. 8 is a side view of the frame of the prosthetic heart valve of FIG. 7.

The outer layers 442 can be secured to the frame 12, such as by suturing the outer peripheral edges 432 to struts 208 with stitching 448 (FIGS. 24 and 25). As mentioned above, the outer peripheral edges 432 of the commissure attachment member 431 can generally correspond to the shape of a closed cell of the frame 202. For example, as shown in FIG. 8, the frame 202 in the illustrated example comprises a plurality of generally diamond-shaped cells 214, each of which is formed by struts 208a, 208b, 208c, and 208d. Stitching 448 can be used to suture the outer peripheral edges 432 of the commissure attachment member 431 to struts 208a, 208b, 208c, and 208d forming a closed cell 214. The commissure attachment member 431 can further include an upper tab 450 and a lower tab 452 projecting from the upper and lower edges of the central portion (FIG. 23). Stitching 448 can also be used suture the upper tab 450 an apex 254 formed by the intersection of struts 208a, 208c and to suture the lower tab 452 to a strut junction 256 formed by the intersection of struts 208b, 208d (FIGS. 7 and 8).

Additional details regarding the method for forming commissures 498 and securing them to the frame 202 of the prosthetic heart valve are described in U.S. Patent Publication No. 2018/0028310, which is incorporated herein by reference.

In some examples, after securing the valvular structure 204 to the frame 202, as described above, an outer sealing member 454 can be mounted around an outer surface 456 of the frame 202 (FIGS. 12 and 22). For example, as shown in FIG. 22 by arrow 457, the outer sealing member 454 can be slid over the exterior of the frame 202 to cover at least a portion of the connecting skirts 410 arranged on the inside of the frame 202. In some examples, as shown in FIG. 12, the outer sealing member 454 can then be 458 secured to the outer surface 456 of the frame 202 and the connecting skirts 410 via one or more sutures 458 (or other fastening members). As an example, FIG. 22 shows a dashed outline 495 around a portion of struts and the connecting skirts 410 to which the outer sealing member 454 can be secured via the one or more sutures 458. In some examples, additional sutures or fasteners can secure portions of the outer sealing member 454 directly to struts 208 of the frame 202 (e.g., top and bottom portions or edges of the outer sealing member 454).

In this way, leaflets of a valvular structure can be attached to a frame of a prosthetic heart valve using one or more connecting skirts. For example, a central portion and side base portions of a connecting skirt can be secured directly to a cusp edge portion of a corresponding leaflet and the central portion and side base portions of the connecting skirt can be secured directly to struts of the frame, thereby securing the attached leaflet to the frame. Each connecting skirt can further include side extension portions that extend across struts of the frame that are disposed between cusp edge portions of adjacent leaflets (e.g., when the valvular structure is attached to the frame, as described above). As a result, the side extension portions of the connecting skirts can cover inner surfaces of the struts and apices at the inflow end of the frame that are otherwise uncovered by the leaflets. Thus, when the prosthetic heart valve is radially compressed onto and around an inflatable balloon of a delivery apparatus, the extension portions of the connecting skirts can serve as a protective barrier between the balloon and apices and struts of the frame. As a result, a longevity and effectiveness (e.g., ability to inflate) of the balloon can be increased.

Delivery Techniques

For implanting a prosthetic valve within the native aortic valve via a transfemoral delivery approach, the prosthetic valve is mounted in a radially compressed state along the distal end portion of a delivery apparatus. The prosthetic valve and the distal end potion of the delivery apparatus are inserted into a femoral artery and are advanced into and through the descending aorta, around the aortic arch, and through the ascending aorta. The prosthetic valve is positioned within the native aortic valve and radially expanded (e.g., by inflating a balloon, actuating one or more actuators of the delivery apparatus, or deploying the prosthetic valve from a sheath to allow the prosthetic valve to self-expand). Alternatively, a prosthetic valve can be implanted within the native aortic valve in a transapical procedure, whereby the prosthetic valve (on the distal end portion of the delivery apparatus) is introduced into the left ventricle through a surgical opening in the chest and the apex of the heart and the prosthetic valve is positioned within the native aortic valve. Alternatively, in a transaortic procedure, a prosthetic valve (on the distal end portion of the delivery apparatus) are introduced into the aorta through a surgical incision in the ascending aorta, such as through a partial J-sternotomy or right parasternal mini-thoracotomy, and then advanced through the ascending aorta toward the native aortic valve.

For implanting a prosthetic valve within the native mitral valve via a transseptal delivery approach, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, into the right atrium, across the atrial septum (through a puncture made in the atrial septum), into the left atrium, and toward the native mitral valve. Alternatively, a prosthetic valve can be implanted within the native mitral valve in a transapical procedure, whereby the prosthetic valve (on the distal end portion of the delivery apparatus) is introduced into the left ventricle through a surgical opening in the chest and the apex of the heart and the prosthetic valve is positioned within the native mitral valve.

For implanting a prosthetic valve within the native tricuspid valve, the prosthetic valve is mounted in a radially compressed state along the distal end portion of a delivery apparatus. The prosthetic valve and the distal end portion of the delivery apparatus are inserted into a femoral vein and are advanced into and through the inferior vena cava, and into the right atrium, and the prosthetic valve is positioned within the native tricuspid valve. A similar approach can be used for implanting the prosthetic valve within the native pulmonary valve or the pulmonary artery, except that the prosthetic valve is advanced through the native tricuspid valve into the right ventricle and toward the pulmonary valve/pulmonary artery.

Another delivery approach is a transatrial approach whereby a prosthetic valve (on the distal end portion of the delivery apparatus) is inserted through an incision in the chest and an incision made through an atrial wall (of the right or left atrium) for accessing any of the native heart valves. Atrial delivery can also be made intravascularly, such as from a pulmonary vein. Still another delivery approach is a transventricular approach whereby a prosthetic valve (on the distal end portion of the delivery apparatus) is inserted through an incision in the chest and an incision made through the wall of the right ventricle (typically at or near the base of the heart) for implanting the prosthetic valve within the native tricuspid valve, the native pulmonary valve, or the pulmonary artery.

In all delivery approaches, the delivery apparatus can be advanced over a guidewire previously inserted into a patient's vasculature. Moreover, the disclosed delivery approaches are not intended to be limited. Any of the prosthetic valves disclosed herein can be implanted using any of various delivery procedures and delivery devices known in the art.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve comprising: an annular frame comprising an inflow end and an outflow end and being radially collapsible and expandable between a radially collapsed configuration and a radially expanded configuration, wherein the frame comprises a plurality of struts; and a valvular structure mounted within the frame and comprising a plurality of leaflets, wherein each leaflet comprises opposing tabs on opposite sides of the leaflet and a cusp edge portion between the tabs; wherein the cusp edge portion of each leaflet is connected to the frame by a connecting skirt, wherein each connecting skirt comprises a central portion and opposing side base portions on opposite sides of the central portion that are connected to each of and disposed between the frame and the cusp edge portion of the leaflet, and wherein each connecting skirt further comprises side extension portions that extend outward from the cusp edge portion of the leaflet and across struts of the frame that are disposed between cusp edge portions of adjacent leaflets.

Example 2. The prosthetic heart valve of any example herein, particularly example 1, wherein the plurality of struts form a plurality of apices at the inflow end and the outflow end of the frame and wherein each side extension portion of each connecting skirt extends across the struts of the frame that are disposed between cusp edge portion of adjacent leaflets such that an inner surface of each apex of the plurality of apices that are disposed at the inflow end of the frame, between adjacent leaflets, is covered by a corresponding side extension portion of a corresponding connecting skirt.

Example 3. The prosthetic heart valve of any example herein, particularly example 1 or example 2, wherein each side extension portion extends across one or more cells of a plurality of open cells defined by the plurality of struts, the one or more cells uncovered by the plurality of leaflets.

Example 4. The prosthetic heart valve of any example herein, particularly any one of examples 1-3, wherein each side extension portion is secured to an adjacent side extension portion of an adjacent connecting skirt.

Example 5. The prosthetic heart valve of any example herein, particularly example 4, wherein each side extension portion includes one or more apertures disposed in an angled edge of the side extension portion and wherein each side extension portion is secured to the adjacent side extension portion of the adjacent connecting skirt via one or more sutures extending through the one or more apertures.

Example 6. The prosthetic heart valve of any example herein, particularly any one of examples 1-5, wherein each connecting skirt includes one or more notches disposed between the central portion and the side base portions that are configured to allow the side base portions to bend relative to the central portion.

Example 7. The prosthetic heart valve of any example herein, particularly any one of examples 1-6, wherein each side extension portion of each connecting skirt is triangular and formed by two angled edges that extend outward from opposite ends of a respective side base portion of the side base portions of the connecting skirt.

Example 8. The prosthetic heart valve of any example herein, particularly any one of examples 1-7, wherein each connecting skirt includes a plurality of rows of apertures disposed in and extending across the side base portions and the central portion.

Example 9. The prosthetic heart valve of any example herein, particularly example 8, wherein, for each leaflet, the central portion and side base portions of the connecting skirt are arranged along and secured to the cusp edge portion of the leaflet via one or more sutures extending through a first two rows of the plurality of rows of apertures.

Example 10. The prosthetic heart valve of any example herein, particularly example 9, wherein, for each leaflet, the central portion and side base portions of the connecting skirt secured to the leaflet are further secured to struts of the plurality of struts of the frame via one or more sutures extending through a second two rows of the plurality of rows of apertures.

Example 11. The prosthetic heart valve of any example herein, particularly example 10, wherein the central portion and the side base portions are folded over lengthwise along the cusp edge portion of the leaflet to form two folded portions such that the first two rows overlap one another and the second two rows overlap one another.

Example 12. The prosthetic heart valve of any example herein, particularly any one of examples 1-11, wherein each leaflet and each connecting skirt are secured to each adjacent leaflet and each adjacent connecting skirt, along cusp edge portions of the plurality of leaflets, to form the valvular structure.

Example 13. The prosthetic heart valve of any example herein, particularly any one of examples 1-12, wherein each tab of the opposing tabs of each leaflet is paired with an adjacent tab of an adjacent leaflet to form a plurality of commissures that are connected to the frame, at the outflow end of the frame.

Example 14. The prosthetic heart valve of any example herein, particularly example 13, wherein each side extension portion covers an inner surface of struts of the frame that are disposed between struts of the frame that are connected to a commissure of the plurality of commissures and the inflow end of the frame.

Example 15. The prosthetic heart valve of any example herein, particularly any one of examples 1-14, further comprising an outer sealing member mounted on an outer surface of the frame and secured to each connecting skirt.

Example 16. The prosthetic heart valve of any example herein, particularly example 15, wherein the outer sealing member extends from the inflow end of the frame, toward the outflow end of the frame.

Example 17. A prosthetic heart valve comprising: an annular frame comprising an inflow end and an outflow end and being radially collapsible and expandable between a radially collapsed configuration and a radially expanded configuration, wherein the frame comprises a plurality of struts; a valvular structure mounted within the frame and comprising a plurality of leaflets, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame; and a plurality of connecting skirts, each connecting skirt comprising side base portions and a central portion connected to each of the cusp edge portion of a corresponding leaflet of the plurality of leaflets and struts of the frame, each connecting skirt further comprising side extension portions that extend outward and away from the cusp edge portion, wherein each side extension portion of each connecting skirt extends across struts of the frame, between cusp edge portions of adjacent leaflets and connects to an adjacent side extension portion of an adjacent connecting skirt.

Example 18. The prosthetic heart valve of any example herein, particularly example 17, wherein each side extension portion connects to the adjacent side extension portion of the adjacent connecting skirt from a strut junction to which a corresponding commissure of the plurality of commissures is connected, to the inflow end of the frame.

Example 19. The prosthetic heart valve of any example herein, particularly example 17 or example 18, wherein each side extension portion extends from the cusp edge portion of a corresponding leaflet to the inflow end of the frame and covers an inner surface of an apex of the frame at the inflow end.

Example 20. The prosthetic heart valve of any example herein, particularly any one of examples 17-19, wherein each connecting skirt includes two side base portions, each arranged on an opposite side of the central portion, and two side extension portions, each side extension portion extending outward from a corresponding side base portion of the two side base portions.

Example 21. The prosthetic heart valve of any example herein, particularly example 20, wherein each side extension portion is triangular.

Example 22. The prosthetic heart valve of any example herein, particularly example 20 or example 21, wherein the two side base portions and central portion of each connecting skirt are rectangular.

Example 23. The prosthetic heart valve of any example herein, particularly any one of examples 20-22, wherein for each connecting skirt, the two side base portions and the central portion form a straight, first edge of the connecting skirt and wherein the two side extension portions form a non-straight, second edge arranged opposite the first edge, the non-straight second edge having multiple angled edges.

Example 24. The prosthetic heart valve of any example herein, particularly any one of examples 20-23, wherein each side extension portion of each connecting skirt includes an angled edge extending from a free end of the corresponding side base portion and wherein each side extension portion includes one or more apertures disposed therein, adjacent to the angled edge.

Example 25. The prosthetic heart valve of any example herein, particularly example 24, wherein each side extension portion at least partially overlaps and is connected to the adjacent side extension portion of the adjacent connecting skirt by one or more sutures extending through the one or more apertures in each of the side extension portion and the adjacent side extension portion.

Example 26. The prosthetic heart valve of any example herein, particularly any one of examples 20-25, wherein each connecting skirt includes a plurality of rows of apertures in the central portion and two side base portions and wherein each row of apertures includes a plurality of apertures spaced apart from one another and extending from a free end of one side base portion of the two side base portions to another side base portion of the two side base portions.

Example 27. The prosthetic heart valve of any example herein, particularly example 26, wherein the plurality of rows of apertures includes four rows of apertures that are spaced apart from one another and wherein the central portion and the two side base portions are folded lengthwise and arranged along the cusp edge portion of the corresponding leaflet such that two fold layers are formed and a first and fourth row of apertures of the four rows of apertures overlap one another and a second and third row of apertures of the four rows of apertures overlap one another.

Example 28. The prosthetic heart valve of any example herein, particularly example 27, wherein each connecting skirt is secured to the cusp edge portion of the corresponding leaflet via one or more sutures that extend through the second and third row of apertures.

Example 29. The prosthetic heart valve of any example herein, particularly example 28, wherein each connecting skirt is secured to the struts of the frame via one or more sutures that extend through the first and fourth row of apertures.

Example 30. The prosthetic heart valve of any example herein, particularly any one of examples 20-29, wherein each connecting skirt includes slits that partially separate the two side base portions from the central portion to allow the connecting skirt to be aligned along the cusp edge portion of the corresponding leaflet.

Example 31. The prosthetic heart valve of any example herein, particularly example 30, wherein the cusp edge portion of each leaflet includes a central portion and two angled side edge portions that extend from either side of the central portion to a respective one of the opposing tabs.

Example 32. The prosthetic heart valve of any example herein, particularly any one of examples 17-31, wherein the plurality of struts form a plurality of open cells and wherein each commissure of the plurality of commissures is disposed across a cell of the plurality of open cells that is disposed at the outflow end of the frame.

Example 33. The prosthetic heart valve of any example herein, particularly example 32, wherein the side extension portions of adjacent connecting skirts extend across cells of the plurality of open cells that are disposed between the cell including the commissure and the inflow end of the frame.

Example 34. The prosthetic heart valve of any example herein, particularly any one of examples 17-33, further comprising an outer sealing member mounted around an outer surface of the frame and secured to the struts of the frame and the plurality of connecting skirts, the plurality of connecting skirts mounted around an inner surface of the frame.

Example 35. A method of assembling a prosthetic heart valve comprising a plurality of leaflets, the method comprising: forming a plurality of leaflet assemblies with the plurality of leaflets, wherein each leaflet assembly is formed by: securing a central portion and side base portions of a connecting skirt to a cusp edge portion of a leaflet, wherein each connecting skirt comprises two side portions, one arranged on either side of the central portion, and wherein each side portion comprises a corresponding side base portion of the side base portions and a side extension portion extending outward and away from the corresponding side base portion; securing each connecting skirt to a frame of the prosthetic heart valve, the frame comprising a plurality of interconnected and angled struts, the securing including: securing the central portion and side base portions of the connecting skirt to a first portion of struts of the plurality of struts; and extending each side extension portion of the connecting skirt across a second portion of struts of the plurality of struts that are disposed between cusp edge portions of adjacent leaflets and securing each side extension portion to an adjacent side extension portion of an adjacent connecting skirt.

Example 36. The method of any example herein, particularly example 35, wherein securing the central portion and side base portion of the connecting skirt to the cusp edge portion of the leaflet includes folding the central portion and side base portion lengthwise to form two fold layers and securing the two fold layers to the cusp edge portion of the leaflet.

Example 37. The method of any example herein, particularly example 36, wherein each connecting skirt includes a plurality of rows of apertures extending along the central portion and side base portions and wherein securing the two fold layers to the cusp edge portion of the leaflet includes extending one or more sutures through the cusp edge portion of the leaflet and overlapping apertures of a first two rows of apertures of the plurality of rows of apertures, along a length of the cusp edge portion, to secure the central portion and the side base portions of the connecting skirt to the cusp edge portion of the leaflet.

Example 38. The method of any example herein, particularly example 36 or example 37, wherein during the securing the central portion and side base portions of the connecting skirt to the cusp edge portion of the leaflet, each side extension portion of the connecting skirt extends outward from the two fold layers and across an inner surface of the leaflet.

Example 39. The method of any example herein, particularly any one of examples 36-38, wherein securing the central portion and side base portions of the connecting skirt to the first portion of struts includes securing the two fold layers of the connecting skirt to the first portion of struts via one or more sutures extending through overlapping apertures of a second two rows of apertures of the plurality of rows of apertures and around the first portion of struts, along a length of the cusp edge portion of the leaflet Example 40. The method of any example herein, particularly any one of examples 35-39, wherein extending each side extension portion of the connecting skirt across the second portion of struts includes covering inner surfaces of the second portion of struts and an apex of the frame that is arranged at an inflow end of the frame with the side extension portion.

Example 41. The method of any example herein, particularly any one of examples 35-39, wherein securing each side extension portion to the adjacent side extension portion of the adjacent connecting skirt includes securing overlapping portions of the side extension portion and the adjacent side extension portion together via one or more sutures.

Example 42. The method of any example herein, particularly example 41, wherein securing the overlapping portions together includes extending one or more sutures through the overlapping portions, from a strut junction where the cusp edge portions of the adjacent leaflets meet to an inflow end of the frame.

Example 43. The method of any example herein, particularly any one of examples 35-42, further comprising, after forming the plurality of leaflet assemblies, connecting the plurality of leaflet assemblies together to form a valvular structure, arranging the valvular structure within an interior of the frame, and then securing each connecting skirt to the frame.

Example 44. The method of any example herein, particularly example 43, wherein connecting the plurality of leaflet assemblies together to form the valvular structure includes extending one or more sutures through each connecting skirt and cusp edge portion of each leaflet to form a stitching line along and between each cusp edge portion of each leaflet of the valvular structure.

Example 45. The method of any example herein, particularly any one of examples 35-44, wherein each leaflet comprises opposing tabs on opposite sides of the cusp edge portion of the leaflet and further comprising pairing each tab with an adjacent tab of an adjacent leaflet to form a commissure and securing the commissure to the frame.

Example 46. The method of any example herein, particularly example 45, wherein securing the commissure to the frame includes securing the commissure to a third portion of struts of the plurality of struts that form a cell at an outflow end of the frame.

Example 47. The method of any example herein, particularly example 45 or example 46, wherein the first portion of struts are struts extending at an angle from a first commissure to an inflow end of the frame and at an angle from the inflow end to a second commissure.

Example 48. The method of any example herein, particularly any one of examples 45-47, wherein securing each side extension portion to the adjacent side extension portion of the adjacent connecting skirt includes securing each side extension portion to the adjacent side extension portion via extending one or more sutures through overlapping portions of the side extension portion and the adjacent side extension portion which extend from the commissure to an inflow end of the frame.

Example 49. The method of any example herein, particularly any one of examples 35-48, further comprising mounting an outer sealing member around an outer surface of the frame and securing the outer sealing member to struts of the frame and each connecting skirt.

Example 50. A prosthetic heart valve comprising: an annular frame comprising an inflow end and an outflow end and being radially collapsible and expandable between a radially collapsed configuration and a radially expanded configuration, wherein the frame comprises a plurality of struts; a valvular structure mounted within the frame and comprising a plurality of leaflets, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame; a plurality of connecting skirts, each connecting skirt comprising a base portion connected to each of the cusp edge portion of a corresponding leaflet of the plurality of leaflets and struts of the frame, each connecting skirt further comprising extension portions that extend outward and away from the cusp edge portion and cover inner surfaces of struts of the frame disposed between cusp edge portions of adjacent leaflets; and an outer sealing member mounted around an outer surface of the frame and secured to the struts of the frame and the plurality of connecting skirts, the plurality of connecting skirts mounted around an inner surface of the frame.

Example 51. The prosthetic heart valve of any example herein, particularly example 50, wherein a portion of the struts of the frame covered by the extension portions of each leaflet form apices at the inflow end of the frame.

Example 52. The prosthetic heart valve of any example herein, particularly any one of examples 50 or example 51, wherein the base portion of each connecting skirt comprises a central portion and opposing side base portions disposed on either side of the central portion and wherein each extension portion of the connecting skirt extends outward from a respective side base portion of the opposing side base portions.

Example 53. The prosthetic heart valve of any example herein, particularly any one of examples 50-52, wherein the extension portions are triangular.

Example 54. The prosthetic heart valve of any example herein, particularly any one of examples 50-53, wherein each extension portion of each connecting skirt is attached to an adjacent extension portion of an adjacent connecting skirt.

Example 55. The prosthetic heart valve of any example herein, particularly example 54, wherein each extension portion is attached to the adjacent extension portion in a region of the frame that is disposed between, in an axial direction that is relative to a central longitudinal axis of the frame, a commissure of the plurality of commissures and the inflow end of the frame.

In view of the many possible examples to which the principles of the disclosed technology may be applied, it should be recognized that the illustrated examples are only examples of the disclosed technology and should not be taken as limiting the scope of the claimed subject matter. Rather, the scope of the claimed subject matter is defined by the following claims and their equivalents.

We claim:

1. A prosthetic heart valve comprising:
   an annular frame comprising an inflow end and an outflow end and being radially collapsible and expandable between a radially collapsed configuration and a radially expanded configuration, wherein the frame comprises a plurality of struts; and
   a valvular structure mounted within the frame and comprising a plurality of leaflets, wherein each leaflet comprises opposing tabs on opposite sides of the leaflet and a cusp edge portion between the tabs;
   wherein the cusp edge portion of each leaflet is connected to the frame by a connecting skirt, wherein each connecting skirt comprises a central portion and opposing side base portions on opposite sides of the central portion that are connected to each of and disposed between the frame and the cusp edge portion of the leaflet, and wherein each connecting skirt further comprises side extension portions that extend outward from the cusp edge portion of the leaflet and across struts of the frame that are disposed between cusp edge portions of adjacent leaflets; and
   wherein the plurality of struts form a plurality of apices at the inflow end and the outflow end of the frame and wherein each side extension portion of each connecting skirt extends across the struts of the frame that are disposed between cusp edge portions of adjacent leaflets such that an inner surface of each apex of the plurality of apices that are disposed at the inflow end of the frame, between adjacent leaflets, is covered by a corresponding side extension portion of a corresponding connecting skirt.

2. The prosthetic heart valve of claim 1, wherein each side extension portion extends across one or more cells of a plurality of open cells defined by the plurality of struts, the one or more cells uncovered by the plurality of leaflets.

3. The prosthetic heart valve of claim 1, wherein each connecting skirt includes one or more notches disposed between the central portion and the side base portions that are configured to allow the side base portions to bend relative to the central portion.

4. The prosthetic heart valve of claim 1, wherein each side extension portion of each connecting skirt is triangular and formed by two angled edges that extend outward from opposite ends of a respective side base portion of the side base portions of the connecting skirt.

5. The prosthetic heart valve of claim 1, wherein each connecting skirt includes a plurality of rows of apertures disposed in and extending across the side base portions and the central portion, and wherein, for each leaflet, the central portion and side base portions of the connecting skirt are arranged along and secured to the cusp edge portion of the leaflet via one or more sutures extending through a first row of the plurality of rows of apertures.

6. The prosthetic heart valve of claim 5, wherein, for each leaflet, the central portion and side base portions of the connecting skirt secured to the leaflet are further secured to struts of the plurality of struts of the frame via one or more sutures extending through a second row of the plurality of rows of apertures.

7. The prosthetic heart valve of claim 1, wherein each tab of the opposing tabs of each leaflet is paired with an adjacent tab of an adjacent leaflet to form a plurality of commissures that are connected to the frame, at the outflow end of the frame.

8. The prosthetic heart valve of claim 7, wherein each side extension portion covers an inner surface of struts of the frame that are disposed between struts of the frame that are connected to a commissure of the plurality of commissures and the inflow end of the frame.

9. The prosthetic heart valve of claim 1, further comprising an outer sealing member mounted on an outer surface of the frame and secured to each connecting skirt.

10. A prosthetic heart valve comprising:
an annular frame comprising an inflow end and an outflow end and being radially collapsible and expandable between a radially collapsed configuration and a radially expanded configuration, wherein the frame comprises a plurality of struts; and
a valvular structure mounted within the frame and comprising a plurality of leaflets, wherein each leaflet comprises opposing tabs on opposite sides of the leaflet and a cusp edge portion between the tabs;
wherein the cusp edge portion of each leaflet is connected to the frame by a connecting skirt, wherein each connecting skirt comprises a central portion and opposing side base portions on opposite sides of the central portion that are connected to each of and disposed between the frame and the cusp edge portion of the leaflet, and wherein each connecting skirt further comprises side extension portions that extend outward from the cusp edge portion of the leaflet and across struts of the frame that are disposed between cusp edge portions of adjacent leaflets; and
wherein each side extension portion is secured to an adjacent side extension portion of an adjacent connecting skirt.

11. A method of assembling a prosthetic heart valve comprising a plurality of leaflets, comprising:
forming a plurality of leaflet assemblies with the plurality of leaflets, wherein each leaflet assembly is formed by:
securing a central portion and side base portions of a connecting skirt to a cusp edge portion of a leaflet, wherein each connecting skirt comprises two side portions, one arranged on either side of the central portion, and wherein each side portion comprises a corresponding side base portion of the side base portions and a side extension portion extending outward and away from the corresponding side base portion;
securing each connecting skirt to a frame of the prosthetic heart valve, the frame comprising a plurality of interconnected and angled struts, the securing including:
securing the central portion and side base portions of the connecting skirt to a first portion of struts of the plurality of struts; and
extending each side extension portion of the connecting skirt across a second portion of struts of the plurality of struts that are disposed between cusp edge portions of adjacent leaflets and securing each side extension portion to an adjacent side extension portion of an adjacent connecting skirt.

12. The method of claim 11, wherein each connecting skirt includes a plurality of rows of apertures extending along the central portion and side base portions, and wherein securing the central portion and side base portions to the cusp edge portion of the leaflet includes extending one or more sutures through the cusp edge portion of the leaflet and a first row of apertures of the plurality of rows of apertures, along a length of the cusp edge portion, to secure the central portion and the side base portions of the connecting skirt to the cusp edge portion of the leaflet.

13. The method of claim 12, wherein securing the central portion and side base portions of the connecting skirt to the first portion of struts includes securing the central portion and side base portions of the connecting skirt to the first portion of struts via one or more sutures extending through a second row of apertures of the plurality of rows of apertures and around the first portion of struts, along a length of the cusp edge portion of the leaflet.

14. The method of claim 11, wherein extending each side extension portion of the connecting skirt across the second portion of struts includes covering inner surfaces of the second portion of struts and an apex of the frame that is arranged at an inflow end of the frame with the side extension portion.

15. The method of claim 11, wherein securing each side extension portion to the adjacent side extension portion of the adjacent connecting skirt includes securing overlapping portions of the side extension portion and the adjacent side extension portion together via one or more sutures.

16. The method of claim 11, further comprising, after forming the plurality of leaflet assemblies, connecting the plurality of leaflet assemblies together to form a valvular structure, arranging the valvular structure within an interior of the frame, and then securing each connecting skirt to the frame.

17. A prosthetic heart valve comprising:
an annular frame comprising an inflow end and an outflow end and being radially collapsible and expandable between a radially collapsed configuration and a radially expanded configuration, wherein the frame comprises a plurality of struts;
a valvular structure mounted within the frame and comprising a plurality of leaflets, wherein each leaflet comprises opposing tabs on opposite sides of the leaflet and a cusp edge portion between the tabs, wherein each tab is paired with an adjacent tab of an adjacent leaflet to form a plurality of commissures that are connected to the frame;
a plurality of connecting skirts, each connecting skirt comprising a base portion connected to each of the cusp edge portion of a corresponding leaflet of the plurality of leaflets and struts of the frame, each connecting skirt further comprising extension portions that extend outward and away from the cusp edge portion and cover inner surfaces of struts of the frame disposed between cusp edge portions of adjacent leaflets; and
an outer sealing member mounted around an outer surface of the frame and secured to the struts of the frame and the plurality of connecting skirts, the plurality of connecting skirts mounted around an inner surface of the frame.

18. The prosthetic heart valve of claim 17, wherein a portion of the struts of the frame covered by the extension portions of each connecting skirt form apices at the inflow end of the frame.

19. The prosthetic heart valve of claim 17, wherein the base portion of each connecting skirt comprises a central portion and opposing side base portions disposed on either side of the central portion, and wherein each extension portion of the connecting skirt extends outward from a respective side base portion of the opposing side base portions.

20. The prosthetic heart valve of claim 17, wherein each extension portion of each connecting skirt is attached to an adjacent extension portion of an adjacent connecting skirt, and wherein each extension portion is attached to the adjacent extension portion in a region of the frame that is disposed between, in an axial direction that is relative to a central longitudinal axis of the frame, a commissure of the plurality of commissures and the inflow end of the frame.

\* \* \* \* \*